US010716712B2

(12) United States Patent
Turner et al.

(10) Patent No.: US 10,716,712 B2
(45) Date of Patent: Jul. 21, 2020

(54) ABSORBENT ARTICLES WITH ACTIVATION-FRIENDLY LAMINATES

(71) Applicant: The Procter & Gamble Company, Cincinnati, OH (US)

(72) Inventors: Robert Haines Turner, Cincinnati, OH (US); Todd Leon Mansfield, Cincinnati, OH (US); Torsten Lindner, Kronberg (DE); Matthias Morand, Bad Soden (DE)

(73) Assignee: The Procter & Gamble Company, Cincinnati, OH (US)

( * ) Notice: Subject to any disclaimer, the term of this patent is extended or adjusted under 35 U.S.C. 154(b) by 586 days.

(21) Appl. No.: 14/302,473

(22) Filed: Jun. 12, 2014

(65) Prior Publication Data

US 2014/0378924 A1 Dec. 25, 2014

Related U.S. Application Data

(60) Provisional application No. 61/837,286, filed on Jun. 20, 2013.

(51) Int. Cl.
| | | |
|---|---|---|
| *A61F 13/15* | (2006.01) | |
| *A61F 13/20* | (2006.01) | |
| *B32B 7/12* | (2006.01) | |
| *B32B 27/12* | (2006.01) | |

(Continued)

(52) U.S. Cl.
CPC .. *A61F 13/15203* (2013.01); *A61F 13/15699* (2013.01); *A61F 13/4902* (2013.01); *B32B 5/022* (2013.01); *B32B 7/12* (2013.01); *B32B 27/12* (2013.01); *A61F 2013/15284* (2013.01);

(Continued)

(58) Field of Classification Search
CPC ............ A61F 13/15203; A61F 13/4902; A61F 2013/15284; B32B 2307/51; B32B 2555/02; B32B 27/12; B32B 7/12
See application file for complete search history.

(56) References Cited

U.S. PATENT DOCUMENTS

| 3,624,272 A | 11/1971 | Favreau |
|---|---|---|
| 3,645,992 A | 2/1972 | Elston |
| 3,848,594 A | 11/1974 | Buell |

(Continued)

FOREIGN PATENT DOCUMENTS

| EP | 0410412 B1 | 1/1994 |
|---|---|---|
| EP | 0422108 B1 | 8/1994 |

(Continued)

OTHER PUBLICATIONS

International Search Report, PCT/US2014/042106, dated Sep. 19, 2014, 9 pages.

*Primary Examiner* — Michele M Kidwell
(74) *Attorney, Agent, or Firm* — Daniel S. Albrecht; Kathleen Y. Carter

(57) ABSTRACT

An absorbent article comprising at least one stretchable laminate comprising a first nonwoven, a second nonwoven, and an elastic film therebetween, wherein each of the first and second nonwovens is adhesively bonded to the film by a hot melt adhesive; wherein the film is no thicker than about 60 micrometers; wherein at least one of the nonwovens is spunbonded; wherein the laminate is activated with a minimum of about 290% applied strain and a minimum strain rate of about 850/sec; and wherein the laminate is substantially free from pinholes.

16 Claims, 13 Drawing Sheets

(51) Int. Cl.
 *A61F 13/49* (2006.01)
 *B32B 5/02* (2006.01)
(52) U.S. Cl.
 CPC ....... *B32B 2307/51* (2013.01); *B32B 2555/00* (2013.01); *B32B 2555/02* (2013.01)

(56) References Cited

U.S. PATENT DOCUMENTS

| | | |
|---|---|---|
| 3,860,003 A | 1/1975 | Buell |
| 4,116,892 A | 9/1978 | Schwarz |
| 4,379,190 A | 4/1983 | Schenick |
| 4,515,595 A | 5/1985 | Kievet et al. |
| 4,662,875 A | 5/1987 | Hirotsu et al. |
| 4,699,622 A | 10/1987 | Toussant et al. |
| 4,710,189 A | 12/1987 | Lash |
| 4,798,081 A | 1/1989 | Hazlitt et al. |
| 4,808,178 A | 2/1989 | Aziz |
| 4,834,741 A | 5/1989 | Sabee |
| 4,846,815 A | 7/1989 | Scripps |
| 4,892,536 A | 1/1990 | Desmarais et al. |
| 4,894,060 A | 1/1990 | Nestegard |
| 4,909,803 A | 3/1990 | Aziz et al. |
| 4,921,556 A | 5/1990 | Hakiel et al. |
| 4,937,299 A | 6/1990 | Ewen et al. |
| 4,946,527 A | 8/1990 | Battrell |
| 4,990,147 A | 2/1991 | Freeland |
| 5,037,416 A | 8/1991 | Allen et al. |
| 5,089,321 A | 2/1992 | Chum et al. |
| 5,096,955 A | 3/1992 | Johnston et al. |
| 5,143,679 A * | 9/1992 | Weber ............... A61F 13/15593 264/288.8 |
| 5,151,092 A | 9/1992 | Buell et al. |
| 5,156,793 A | 10/1992 | Buell et al. |
| 5,167,897 A | 12/1992 | Weber et al. |
| 5,218,071 A | 6/1993 | Tsutsui et al. |
| 5,221,274 A | 6/1993 | Buell et al. |
| 5,269,775 A | 12/1993 | Freeland et al. |
| 5,272,236 A | 12/1993 | Lai et al. |
| 5,278,272 A | 1/1994 | Lai et al. |
| 5,422,172 A | 6/1995 | Wu et al. |
| 5,518,801 A | 5/1996 | Chappell et al. |
| 5,554,145 A | 9/1996 | Roe et al. |
| 5,569,234 A | 10/1996 | Buell et al. |
| 5,580,411 A | 12/1996 | Nease et al. |
| 5,650,214 A | 7/1997 | Anderson et al. |
| 5,843,057 A | 12/1998 | McCormack |
| 5,858,292 A | 1/1999 | Dragoo et al. |
| 5,861,074 A | 1/1999 | Wu |
| 6,004,306 A | 12/1999 | Roe et al. |
| 6,120,487 A | 9/2000 | Buell et al. |
| 6,313,372 B1 | 11/2001 | Suzuki |
| 6,428,526 B1 | 8/2002 | Heindel et al. |
| 6,458,877 B1 * | 10/2002 | Ahmed ................. A61L 15/225 524/275 |
| 6,605,172 B1 * | 8/2003 | Anderson ............... B29C 55/18 156/199 |
| 6,645,569 B2 | 11/2003 | Rohrbaugh et al. |
| 6,830,800 B2 | 12/2004 | Curro et al. |
| 6,863,933 B2 | 3/2005 | Rohrbaugh et al. |
| 7,112,621 B2 | 9/2006 | Rohrbaugh et al. |
| 7,199,180 B1 | 4/2007 | Simmons et al. |
| 7,626,073 B2 | 12/2009 | Catalan |
| 7,655,583 B2 | 2/2010 | Marche |
| 7,824,514 B2 | 11/2010 | Venkitaraman et al. |
| 7,938,921 B2 | 5/2011 | Ng et al. |
| 7,959,619 B2 | 6/2011 | Cartier et al. |
| 8,153,238 B2 | 4/2012 | Hall et al. |
| 8,163,833 B2 | 4/2012 | Moeller et al. |
| 8,222,339 B2 * | 7/2012 | Yalvac ................. C09J 153/00 524/543 |
| 8,226,626 B2 | 7/2012 | Turner et al. |
| 8,618,350 B2 | 12/2013 | Mansfield |
| 2003/0060794 A1 | 3/2003 | Olson |
| 2003/0134552 A1 * | 7/2003 | Mehawej ................. C08L 53/00 442/118 |
| 2005/0106980 A1 | 5/2005 | Abed et al. |
| 2005/0215963 A1 * | 9/2005 | Autran ............... A61F 13/15203 604/358 |
| 2005/0215971 A1 * | 9/2005 | Roe ................... A61F 13/49011 604/385.27 |
| 2005/0222546 A1 | 10/2005 | Vargo et al. |
| 2006/0199457 A1 * | 9/2006 | Hall ........................ B32B 5/26 442/327 |
| 2007/0105472 A1 | 5/2007 | Marche |
| 2007/0249254 A1 | 10/2007 | Mansfield |
| 2008/0045917 A1 | 2/2008 | Autran et al. |
| 2008/0233824 A1 | 9/2008 | Abed et al. |
| 2009/0191779 A1 | 7/2009 | Cree |
| 2009/0208703 A1 | 8/2009 | Wennerback et al. |
| 2009/0326503 A1 | 12/2009 | Lakso et al. |
| 2010/0040826 A1 * | 2/2010 | Autran ............... A61F 13/51464 428/113 |
| 2010/0104830 A1 | 4/2010 | Jaeger et al. |
| 2010/0310837 A1 | 12/2010 | Bond et al. |
| 2010/0318054 A1 | 12/2010 | Langdon et al. |
| 2011/0000607 A1 | 1/2011 | Venkitaraman et al. |
| 2011/0203102 A1 | 8/2011 | Trennepohl et al. |
| 2012/0207969 A1 | 8/2012 | Mansfield |
| 2013/0158176 A1 * | 6/2013 | Hu ............................ C09J 5/06 524/274 |

FOREIGN PATENT DOCUMENTS

EP 1150833 B1 4/2006
WO WO 2007/146148 A2 12/2007

\* cited by examiner

ABSORBENT ARTICLES WITH ACTIVATION-FRIENDLY LAMINATES

CROSS-REFERENCE TO RELATED APPLICATIONS

This application claims the benefit of U.S. Provisional Application No. 61/837,286, filed Jun. 20, 2013 which is herein incorporated by reference.

FIELD OF THE INVENTION

Disclosed are absorbent articles comprising stretchable laminates that can withstand a high degree of mechanical activation.

BACKGROUND OF THE INVENTION

Wearable absorbent articles (e.g., taped diapers, pull-on diapers, training pants, sanitary napkins, panty liners, adult incontinence briefs, and bandages) typically offer the benefit of receiving and containing the bodily exudates of a wearer. Disposable varieties of such absorbent articles are commonly known, and can be made with various materials in a number of configurations. Such absorbent articles can include a chassis that defines a waist opening and a pair of leg openings, in addition to or further including side panels, and front or back ear panels.

Absorbent article materials may be made of numerous individual polymeric components that vary not only in terms of their properties, but also in their shape or form. They can be, for example, fibers, strands, fabrics, or films that can possess properties ranging from plastic to elastomeric. In order to produce stretch in materials, elastic materials can be combined while held under large strains with inelastic nonwovens (so called "live stretch"). These have been extensively used in the trade and appreciated for the textured appearance of the gathered nonwovens, but end up using large amounts of nonwoven, and thus may not be the most cost-effective route. An alternative to live stretch constructions are so called "zero-strain" constructions, where mechanical activation is used to apply large strains to a laminate that is comprised of an elastic layer and an inelastic nonwoven layer in order to permanently deform the inelastic layer of the laminate and enable the elastic layer to extend and retract.

In addition, large amounts of glue or adhesives are generally used in assembling the various components into a fully functional chassis. For example, in certain portions, adhesives may be used to attach a thin plastic film used as a fluid barrier to a nonwoven fabric that provides a cloth-like look and feel. Adhesives may be used in stretch elastic back ears or side panels where the adhesively-bonded nonwoven shields against the tacky or blocky nature of the elastic film onto the body side while again providing a soft fabric feel. Or adhesives may be used in the construction of legband or waistband laminates where live stretch strand elastics are sandwiched in between two layers of inelastic nonwovens that gather upon retraction.

One difficulty of working with adhesives is achieving the balance between the right level of adhesive to achieve adequate bond strength with cost while also preventing processing issues such as adhesive burn-through (pinholes) with thin films, adhesive bleed-through with nonwovens, or ruptures that can occur during activation due to the transfer of strain energy between the nonwoven and film. These issues can be difficult as it often requires the use of thicker or more complex nonwoven structures that can impose additional survivability issues during activation. Therefore, there is a continuing need for a way to maximize a laminate's extensibility through activation while still assuring survivability of the laminate.

SUMMARY OF THE INVENTION

An absorbent article comprising at least one stretchable laminate comprising a first nonwoven, a second nonwoven, and an elastic film therebetween, wherein each of the first and second nonwovens is adhesively bonded to the film by a hot melt adhesive; wherein the film is no thicker than about 60 micrometers; wherein at least one of the nonwovens is spunbonded; wherein the laminate is activated with a minimum of about 290% applied strain and a minimum strain rate of about 850/sec; and wherein the laminate is substantially free from pinholes.

DETAILED DESCRIPTION OF THE INVENTION

Definitions

Figure 1:
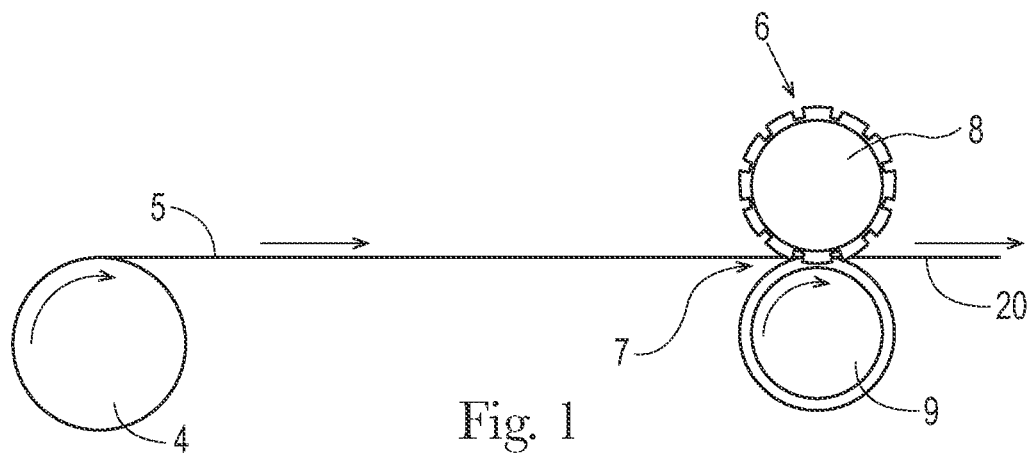
FIG. 1 is a schematic illustration of an exemplary process and apparatus for modifying a web and imparting breathability to a web in accordance with the present invention.

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Activatable nonwoven" refers specifically to nonwovens that have mechanical properties that interact well with films during the activation process. Activatable nonwovens of the present invention give tensile curves (ASTM D882-02, gauge length=5 mm, specimen width=25.4 mm, crosshead speed=2.117 mm/s, deformation direction coinciding with that applied during the activation process) characterized by relatively low maximum forces and relatively large engineering strains. Specifically, if the nonwoven's curve's maximum force point lies below 4 N/cm at an engineering strain value of greater than 100%, then, for the purposes of the present invention, it is deemed to be "activatable."

"Activated" refers to a material which has been mechanically deformed so as to impart elasticity to at least a portion of the material, such as, for example by incremental stretching. As used herein the term "activation" means any process by which tensile strain produced by intermeshing teeth and grooves causes intermediate web sections to stretch or extend. Such processes have been found useful in the production of many articles including breathable films, stretch composites, apertured materials and textured materials. For nonwoven webs, the stretching can cause fiber reorientation, change in fiber denier and/or cross section, a reduction in basis weight, and/or controlled fiber destruction in the intermediate web sections. For example, a common activation method is the process known in the art as ring rolling. U.S. Pat. Nos. 6,830,800, 5,143,679, and 5,167,897 disclose examples of the activation process.

"Adhesive" refers to compositions comprising one or more thermoplastic polymers and typically one or more tackifier resins and a rheology modifier or plasticizer. Adhesives may contain 2% or more of a tackifier resin. An adhesive is generally used to join or bond two or more materials together by applying it to at least one material and then bringing it into contact with at least one other material with sufficient force and for a sufficient duration of time, that the adhesive can wet out or spread on each material to join them together (see definition of "tackifier" below).

"Adhesively bonded" or "adhesively laminated" refers to a laminate wherein an adhesive is used to bond an elastomeric member (e.g., elastomeric film) to a nonwoven(s) or to a second elastomeric member.

"Bicomponent fiber" refers to fibers or filaments consisting of material of two different compositions arranged across the cross-section of the fiber or filament. Each composition is typically delivered by a separate extruder to a spin pack designed to arrange the compositions into arrangements such as sheath-core, side-by-side, segmented pie and islands-in-the-sea. The mutual arrangement of different compositions can be beneficial in tailoring the chemical affinity between a film and a nonwoven in a laminate.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Crystallization rate" refers to the kinetics of crystal nucleation and growth from an adhesive hot melt as it cools. Crystallization rate reflects the route by which a polymer solidifies from a molten, amorphous state. Differential Scanning calorimetry (DSC) may be used according to ASTM D 3418 as described in more detail in the Test Methods to determine crystallization rates of polymers, polymer blends, and formulations comprising polymers useful in adhesives of the present invention.

"Depth of engagement", (DOE), as used herein, means the extent to which intermeshing teeth and grooves of opposing activation members extend into one another.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Disposable" in reference to absorbent articles, means that the absorbent articles are generally not intended to be laundered or otherwise restored or reused as absorbent articles (i.e., they are intended to be discarded after a single use and may be recycled, composted or otherwise discarded in an environmentally compatible manner).

"Disposed" refers to an element being positioned in a particular place with regard to another element. When one group of fibers is disposed on a second group of fibers, the first and second groups of fibers generally form a layered, laminate structure in which at least some fibers from the first and second groups are in contact with each other. In some embodiments, individual fibers from the first and/or second group at the interface between the two groups can be dispersed among the fibers of the adjacent group, thereby forming an at least partially intermingled, entangled fibrous region between the two groups. When a polymeric layer (for example a film), is disposed on a surface (for example a group or layer of fibers), the polymeric layer can be laminated to or printed on the surface.

As used herein, the terms "elastic," "elastomer," and "elastomeric" refer to any material which generally is able to, upon application of a tensile force, extend to an engineering strain of at least 50% without breaking or rupturing, and is able to recover substantially to its original dimensions after the deforming force has been removed.

"Engineering strain" is the change in length of a specimen (in the direction of applied stress or strain) divided by the specimen's original length (William D. Callister Jr., "Materials Science and Engineering: An Introduction", 1985, John Wiley & Sons, Inc. New York, Chichester, Brisbane, Toronto, Singapore). To calculate percent engineering strain, the engineering strain is multiplied by 100. When the word "strain" is used it means "engingeering strain", unless otherwise specified.

"Strain rate" characterizes the speed at which engineering strain is applied to the material and is defined as the first time derivative of engineering strain (v/l0).

"Extensible", "plastic" and "extendibility" (e.g. extensible nonwoven, plastic film or extendibility of the elastomer), means that upon application of a tensile force, the width or length of the material in the relaxed position can be extended or increased, without rupture or breakage. Further, upon release of the applied force, the material shows little recovery, for example, the percent recovery of strain, PRS (as measured by the Percent Strain Recovery Test, PSRT, a modified hysteresis method; see test methods) is less than 80%, or PRS is less than 50%, or PRS is less than 25%, or PRS is less than 10%. It should be noted that the percent recovery of strain (PRS) is equivalent to the percent strain recovery.

"Laminate" means two or more materials that are bonded to one another by methods known in the art, e.g., adhesive bonding, thermal bonding, ultrasonic bonding.

"Machine direction" (also "MD" or "length direction") as applied to a film or nonwoven material, refers to the direction that was parallel to the direction of travel of the film or nonwoven as it was processed in the forming apparatus. The "cross machine direction" (also "CD" or "width direction") refers to the direction perpendicular to the machine direction.

"Side panel," "front ear," "back ear," or "ear panel" refers to that portion of an absorbent article which is disposed adjacent to the outer cover or core or topsheet and connect a front waist edge to a back waist edge. Side panels or front/back ears have tensile properties that enable ease of the application of the article, as well as enabling the article to conform to the wearer's body. Side panels or front/back ears of the present invention may comprise a multilayer laminate. Examples of side panels that may be used in the present invention are described and illustrated in EP 1150833 (referenced as ear panels).

"Tackifier" refers to an adhesive component with a glass transition temperature in the range from about 70° C. to about 150° C. that decreases the melt viscosity of a rubbery polymer and increases the rubbery polymer's glass transition temperature and decreases the rubbery polymer's entanglement density.

Description

In some embodiments, the present invention relates to absorbent articles comprising stretch laminates, such as may be used in, for example, stretchable side portions, back ears, waistbands, and/or stretchable outer covers. The stretchable laminates, which comprise two nonwovens with a film adhesively bonded in between, may achieve novel levels of stretch and elasticity due to harsh mechanical activation. Mechanical activation involves deforming the laminate in order to impart elasticity. In general, the harsher the activation, the more stretch or elasticity that may be achieved.

"Harsh" means higher strains and strain rates applied during activation. However, the harsher the activation, the more likely that holes, or ruptures, will appear in the laminate's elastomeric film. Typically, the nonwoven's deformation acts to transfer strain energy to the film layer with enough concentration of stress to cause the elastomer film to rupture.

Without being bound by theory, it is believed that, in the present invention, novel stretch laminates are achieved due to the realization that when a laminate is activated at a time before the adhesive achieves its full crystallization, as measured by normalized modulus G' (also referred to as normalized G' or G'norm), the strain energy transferred from nonwoven to film is moderated, and the activation may therefore be done more harshly than previously thought without creating pinholes, that is, without destroying the laminate. As a result, the laminates created can have greater extensibility.

Certain hot melt adhesives crystallize or become stiff at a slower rate than others. Adhesives that stiffen at a slower rate, that is, those that have a lower normalized G' at a given time, may allow a greater window of time for harsh activation to occur. A hot melt adhesive will begin cooling and crystallizing the moment that it is applied to a nonwoven on an absorbent article manufacturing line. The present inventors have discovered that activation, when done when the adhesive is less crystallized or less stiff, is less harsh on the laminate, meaning that the activation may be increased without a corresponding increase in pinholes or ruptures. Without being bound by theory, when the laminate comprises an adhesive that has not yet fully crystallized, there is a slight decoupling between the layers of nonwoven and film. If an adhesive crystallizes at a slow enough rate, the activation may occur while the adhesive has not yet fully bonded the nonwovens to the film. Thus, defects that occur in the nonwovens may not necessarily transfer to the film layer.

As such, the present invention discloses stretch laminates that can withstand extreme and harsh activation without the creation of pinholes in the film, which in turn can cause catastrophic failure of the laminate. Further, the present invention discloses stretch laminates that, because they can withstand extreme activation without causing pinholes, can be made more elastic, with more stretch and extensibility than previously achieved.

Adhesives

The hot melt adhesive of the present invention may be any adhesive that allows for the extreme activation and extensibility of a nonwoven-film-nonwoven laminate of the present invention while not producing pinholes or having catastrophic failure of the laminate. The hot melt adhesive should have a slow rate of crystallization, which can be measured via its normalized storage modulus (normalized G' or G'norm), which is calculated as G'norm=[G'(t)–G'(0)]/[G'(inf)–G'(0)] where inf is chosen as 60 minutes.

The hot melt adhesives used in the present invention may be polyolefin-based adhesives. Suitable adhesives may include those that have a low viscosity to allow easy application and mechanical properties that remain as constant as possible up to 50° C. Also, the adhesive's elastic behavior may be as linear as possible or held constant. One exemplary type of adhesive may be those disclosed in U.S. Pat. No. 8,163,833, which is herein incorporated by reference in its entirety, for example comprising from 5% to 40% by weight of at least one copolymer based on ethylene and at least one C3 to C20 α-olefin that is obtainable by metallocene-catalyzed polymerization, 10% to 65% by weight of at least one tackifying resin, from 0% to 35% by weight of a plasticizer, and from 0.01% to 30% by weight of additives and auxiliaries selected from stabilizers, adhesion promoters, fillers or pigments, waxes, and/or other polymers.

Other exemplary polyolefin-based adhesives may include those disclosed in U.S. Ser. Nos. 13/673,277 and 13/673,304, respectively. Such adhesives may include at least one homogeneous ethylene/α-olefin interpolymer which is an interpolymer of ethylene and at least one C3-C20 α-olefin. The term "interpolymer" is used herein to indicate a copolymer, or a terpolymer, or a higher order polymer. That is, at least one other comonomer is polymerized with ethylene to make the interpolymer.

The homogeneous ethylene/α-olefin interpolymer is a homogeneous linear or substantially linear ethylene/α-olefin interpolymer. By the term "homogenous", it is meant that any comonomer is randomly distributed within a given interpolymer molecule and substantially all of the interpolymer molecules have the same ethylene/comonomer ratio within that interpolymer. The melting peak of homogeneous linear and substantially linear ethylene polymers, as obtained using differential scanning calorimetry, will broaden as the density decreases and/or as the number average molecular weight decreases. However, unlike heterogeneous polymers, when a homogeneous polymer has a melting peak greater than 115° C. (such as is the case of polymers having a density greater than 0.940 g/cm3), it does not additionally have a distinct lower temperature melting peak.

In addition or in the alternative, the homogeneity of the polymer may be described by the SCBDI (Short Chain Branching Distribution Index) or CDBI (Composition Distribution Breadth Index), which are defined as the weight percent of the polymer molecules having a conomomer content within 50 percent of the median total molar comonomer content. The SCBDI of a polymer is readily calculated from data obtained from techniques known in the art, such as, for example, temperature rising elution fractionation (abbreviated herein as "TREF"), which is described, for example, in Wild et al., Journal of Polymer Science, Poly. Phys. Ed., Vol. 20, p. 441 (1982), in U.S. Pat. No. 4,798,081 (Hazlitt et al.), or in U.S. Pat. No. 5,089,321 (Chum et al.). It may be preferred that the SCBDI or CDBI for useful homogeneous ethylene/α-olefin interpolymers is greater than 50 percent, or greater than 70 percent, with SCBDI's and CDBI of greater than 90 percent being easily attained.

Useful homogeneous ethylene/α-olefin interpolymers may be characterized as having a narrow molecular weight distribution (Mw/Mn). For useful homogeneous ethylene/α-olefins, the Mw/Mn is from 1.5 to 2.5, or from 1.8 to 2.2, or even about 2.0.

A first polymer may be an interpolymer of ethylene with at least one comonomer selected from the group consisting of C3-C20 α-olefins, non-conjugated dienes, and cycloalkenes. Exemplary C3-C20 α-olefins include propylene, isobutylene, 1-butene, 1-hexene, 4-methyl-1-pentene, 1-heptene, and 1-octene. Suitable C3-C20 α-olefins may include include 1-butene, 1-hexene, 4-methyl-1-pentene, 1-heptene, and 1-octene, or 1-hexene and 1-octene. Exemplary cycloalkenes include cyclopentene, cyclohexene, and cyclooctene. The non-conjugated dienes suitable as comonomers, particularly in the making of ethylene/α-olefin/diene terpolymers, are typically non-conjugated dienes having from 6 to 15 carbon atoms. Representative examples of suitable non-conjugated dienes include:

(a) Straight chain acyclic dienes such as 1,4-hexadiene; 1,5-heptadiene; and 1,6-octadiene;
(b) Branched chain acyclic dienes such as 5-methyl-1,4-hexadiene; 3,7-dimethyl-1,6-octadiene; and 3,7-dimethyl-1,7-octadiene;
(c) Single ring alicyclic dienes such as 4-vinylcyclohexene; 1-allyl-4-isopropylidene cyclohexane; 3-allylcyclopentene; 4-allylcyclohexene; and 1-isopropenyl-4-butenylcyclohexene;
(d) Multi-ring alicyclic fused and bridged ring dienes such as dicyclopentadiene; alkenyl, alkylidene, cycloalkenyl, and cycloalkylidene norbornenes, such as 5-methylene-2-norbornene; 5-methylene-6-methyl-2-norbornene; 5-methylene-6,6-dimethyl-2-norbornene; 5-propenyl-2-norbornene; 5-(3-cyclopentenyl)-2-norbornene; 5-ethylidene-2-norbornene; and 5-cyclohexylidene-2-norbornene.

One suitable conjugated diene is piperylene. Suitable dienes may be selected from the group consisting of 1,4-hexadiene; dicyclopentadiene; 5-ethylidene-2-norbornene; 5-methylene-2-norbornene; 7-methyl-1,6 octadiene; piperylene; and 4-vinylcyclohexene.

The molecular weight of the ethylene/α-olefin interpolymer will be selected on the basis of the desired performance attributes of the adhesive formulation. It may be preferred, however, that the ethylene/α-olefin interpolymer have a number average molecular weight of at least 3,000, preferably at least 5,000. It may be preferred that the ethylene/α-olefin interpolymer have a number average molecular weight of no more than 100,000, or no more than 60,000, or even less than 40,000.

When the ethylene/α-olefin interpolymer has an ultra-low molecular weight, and the like, a number average molecular weight less than 11,000, the ethylene/α-olefin interpolymer leads to a low polymer and formulation viscosity but is characterized by a peak crystallization temperature which is greater than that of corresponding higher molecular weight materials of the same density. In pressure sensitive adhesive applications, the increase in peak crystallization temperature translates to an increased heat resistance. Ultra-low molecular weight ethylene/α-olefin interpolymers are more fully described below.

The density of the ethylene/α-olefin interpolymer will likewise be selected on the basis of the desired performance attributes of the adhesive formulation. It may be preferred, however, that the ethylene/α-olefin interpolymer have a density of at least 0.850 g/cm3, or at least 0.860, or even at least 0.870 g/cm3. It may be preferred that the ethylene/α-olefin interpolymer have a density of no more than 0.965 g/cm3, or no more than 0.900 g/cm3, or no more than 0.890 g/cm3, or even no more than 0.880 g/cm3, or even no more than 0.875 g/cm3.

The ethylene/α-olefin interpolymer may be present in suitable adhesives in an amount greater than 5, or even greater than 10 weight percent. The ethylene/α-olefin interpolymer may generally be present in the suitable adhesive in an amount of not more than 95, or not more than 80, or even not more than 70 weight percent.

The adhesive may include a single homogeneous ethylene/α-olefin interpolymer. In such an embodiment, the suitable homogeneous ethylene/α-olefin interpolymer may have a density ranging from 0.865 g/cm3 to 0.885 g/cm3. When it is desired to prepare an adhesive formulation with a minimal concentration of the homogeneous linear or substantially linear interpolymer, and the like, adhesive formulations containing less than 30 weight percent, or less than 25 weight percent of the homogeneous ethylene/α-olefin interpolymer, the melt index (I2 at 190° C.) of the homogeneous linear or substantially linear interpolymer may be 50 or less, or 30 or less, and or even less than 10 g/10 min. It is believed that adhesive compositions including as little as 5 weight percent of the homogeneous ethylene/α-olefin interpolymer having a melt index less than 0.5 g/10 min. would yield an advantageous performance.

In the case of pressure sensitive adhesives, adhesives may include from 5 to 45 weight percent, or from 10 to 30, or even from 15 to 25 weight percent of a single homogeneous ethylene/α-olefin interpolymer. For other applications, the homogeneous linear or substantially linear interpolymer may be employed at concentrations greater than 30 weight percent and have a melt index of 500 g/10 min or less.

In another embodiment, the first homogeneous ethylene/α-olefin interpolymer may be blended with a second homogeneous ethylene/α-olefin interpolymer, wherein the first and second interpolymers differ in number average molecular weight by at least 5000, or at least 10,000, or even at least 20,000. In this embodiment, the combination of the lower molecular weight and higher molecular weight components will tend to yield an intermediate storage modulus at 25° C. and an improved probe tack.

In addition or in the alternative, the first homogeneous ethylene/α-olefin interpolymer may be blended with a second homogeneous ethylene/α-olefin interpolymer, wherein the first and second interpolymers differ in density by at least 0.005 g/cm3, or even by at least 0.01 g/cm3. In this embodiment, particularly in the case of pressure sensitive adhesives, as the density differential increases, the relative proportion of the higher density interpolymer will typically decrease, as the increased levels of crystallinity would otherwise tend to decrease storage modulus at 25° C. and probe tack to levels which would render them unsuitable for use as pressure sensitive adhesives.

In a particular embodiment, the adhesive may include a blend of two homogeneous ethylene/α-olefin interpolymers, the first interpolymer having a density of 0.870 g/cm3 or less and the second interpolymer having density greater than 0.900 g/cm3. When high cohesive strength is desired, the first and second homogeneous linear or substantially linear interpolymer, may both have relatively low melt indices, and the like, an I2 of less than 30 g/10 min. In contrast, for lower viscosity adhesive compositions, especially those which are sprayable at temperatures less than 325° F. (163° C.), the second homogeneous ethylene/α-olefin interpolymer will have a greater density than the first homogeneous ethylene/α-olefin interpolymer, and may have a melt index greater than 125, or greater than 500, or even greater than 1000 g/10 min.

Homogeneously branched linear ethylene/α-olefin interpolymers may be prepared using polymerization processes (for example, as described by Elston in U.S. Pat. No. 3,645,992) which provide a homogeneous short chain branching distribution. In his polymerization process, Elston uses soluble vanadium catalyst systems to make such polymers. However, others such as Mitsui Petrochemical Company and Exxon Chemical Company have used so-called single site catalyst systems to make polymers having a homogeneous linear structure. U.S. Pat. No. 4,937,299 to Ewen et al. and U.S. Pat. No. 5,218,071, to Tsutsui et al. disclose the use of catalyst systems based on hafnium for the preparation of homogeneous linear ethylene polymers. Homogeneous linear ethylene/α-olefin interpolymers are currently available from Mitsui Petrochemical Company under the trade name "Tafmer" and from Exxon Chemical Company under the trade name "Exact".

Substantially linear ethylene/α-olefin interpolymers are available from The Dow Chemical Company as Affinity (Registered Trademark) polyolefin plastomers and Engage (Registered Trademark) polyolefin elastomers. Substantially linear ethylene/α-olefin interpolymers may be prepared in accordance with the techniques described in U.S. Pat. No. 5,272,236 and in U.S. Pat. No. 5,278,272.

Other semicrystalline polymers that can be useful for adhesives are copolymers of propene with ethylene or alpha olefins comonomers where the crystallizable sequences are of the isopropylene type. The polymers most useful for adhesives have degree of crystallinity of 5-25%. Examples include Vistamaxx (Exxon Mobil Corp., Irving, Tex.); Versify (The Dow Chemical Company, Midland, Mich.); Notio (Mitsui Chemicals America, Inc., Rye Brook, N.Y.), and the like.

Depending on the intended end use for the adhesive, it is often desirable to add at least one compatible polymer in addition to the homogeneous ethylene/α-olefin interpolymer at concentrations up to 25 percent by weight to increase the cohesive strength, improve the sprayability, modify the open time, increase the flexibility, etc. This modifying polymer may be any compatible elastomer, such as a thermoplastic block copolymer, a polyamide, an amorphous or crystalline polyolefin such as polypropylene, polybutylene or polyethylene wherein Mw is greater than 3000; an ethylenic copolymer such as ethylene-vinyl acetate (EVA), ethylene-methyl acrylate, or a mixture thereof. Surprisingly, the homogeneous ethylene/α-olefin interpolymers are also compatible with polyamides, resulting in plasticizer resistant pressure sensitive adhesives. The modifying polymer will typically be used in a relatively low concentration, so as not to detract from the improved properties of the homogeneous ethylene/α-olefin interpolymer. A suitable modifying polymer for increasing the open time and heat resistance may be polybutene-1 copolymer such as Duraflex (Registered Trademark) 8910 (Shell).

Interpolymers of ethylene are those polymers having at least one comonomer selected from the group consisting of vinyl esters of a saturated carboxylic acid wherein the acid moiety has up to 4 carbon atoms, unsaturated mono- or dicarboxylic acids of 3 to 5 carbon atoms, a salt of the unsaturated acid, esters of the unsaturated acid derived from an alcohol having 1 to 8 carbon atoms, and mixtures thereof. Terpolymers of ethylene and these comonomers are also suitable. Ionomers, which are completely or partially neutralized copolymers of ethylene and the acids described above, are discussed in more detail in U.S. Pat. No. 3,264,272. In addition, terpolymers of ethylene/vinyl acetate/carbon monoxide or ethylene/methyl acrylate/carbon monoxide containing up to 15 weight percent carbon monoxide may also be employed. The ethylene to unsaturated carboxylic comonomer weight ratio may be from 95:5 to 40:60, or from 90:10 to 45:50, or even from 85:15 to 60:40. The melt index (I2 at 190° C.) of these modifying interpolymers of ethylene may range from 0.1 to 150, or from 0.3 to 50, or even from 0.7 to 10 g/10 min. Physical properties, principally elongation, are known to decline to lower levels when the ethylene copolymer melt index is above 30 g/10 min.

Suitable ethylene/unsaturated carboxylic acid, salt and ester interpolymers include ethylene/vinyl acetate (EVA) including, but not limited to, the stabilized EVA described in U.S. Pat. No. 5,096,955, incorporated herein by reference; ethylene/acrylic acid (EEA) and its ionomers; ethylene/methacrylic acid and its ionomers; ethylene/methyl acrylate; ethylene/ethyl acrylate; ethylene/isobutyl acrylate; ethylene/n-butyl acrylate; ethylene/isobutyl acrylate/methacrylic acid and its ionomers; ethylene/n-butyl acrylate/methacrylic acid and its ionomers; ethylene/isobutyl acrylate/acrylic acid and its ionomers; ethylene/n-butyl acrylate/acrylic acid and its ionomers; ethylene/methyl methacrylate; ethylene/vinyl acetate/methacrylic acid and its ionomers; ethylene/vinyl acetate/acrylic acid and its ionomers; ethylene/vinyl acetate/carbon monoxide; ethylene/methacrylate/carbon monoxide; ethylene/n-butyl acrylate/carbon monoxide; ethylene/isobutyl acrylate/carbon monoxide; ethylene/vinyl acetate/monoethyl maleate; and ethylene/methyl acrylate/monoethyl maleate. Particularly suitable copolymers are EVA; EAA; ethylene/methyl acrylate; ethylene/isobutyl acrylate; and ethylene/methyl methacrylate copolymers and mixtures thereof. Certain properties, such as tensile elongation, are taught to be improved by certain combinations of these ethylene interpolymers, as described in U.S. Pat. No. 4,379,190. The procedures for making these ethylene interpolymers are well known in the art and many are commercially available.

A suitable adhesive may include from 0 to 95 weight percent of a tackifying resin. Typically, and particularly when it is desired to employ less than 30 weight percent of the homogeneous ethylene/α-olefin interpolymer, the adhesives may include from 10 to 75 weight percent, or from 20 to 60 weight percent tackifier.

In the alternative, in cases where it is desirable to employ at least 30 weight percent of the homogeneous ethylene/α-olefin interpolymer, adhesive formulations which contain minimal tackifier, and the like, less than 30 weight percent tackifier, or less than 25 weight percent tackifier, or even less than 20 weight percent tackifier, or even less than 15 weight percent tackifier, may be advantageous. In such applications, the homogeneous ethylene/α-olefin interpolymer may be provided as a blend with a second homogeneous ethylene/α-olefin interpolymer. In such instances, adhesives containing less than 10 weight percent tackifier, and even adhesives having no tackifier, may exhibit adequate tack.

In general terms, useful tackifying resins may include resins derived from renewable resources such as rosin derivatives including wood rosin, tall oil, gum rosin; rosin esters, natural and synthetic terpenes, and derivatives of such. Aliphatic, aromatic or mixed aliphatic-aromatic petroleum based tackifiers may also be useful in suitable adhesives. Representative examples of useful hydrocarbon resins includes α-methyl styrene resins, branched and unbranched C5 resins, C9 resins, C10 resins, as well as styrenic and hydrogenated modifications of such. Tackifying resins range from being a liquid at 37° C. to having a ring and ball softening point of about 135° C. Solid tackifying resins with a softening point greater than about 100° C., or with a softening point greater than about 130° C. may be useful to improve the cohesive strength of suitable adhesives, particularly when only a single homogeneous ethylene/α-olefin interpolymer is utilized.

For suitable adhesives, a suitable tackifying resin may be predominantly aliphatic. However, tackifying resins with increasing aromatic character may also be useful, particularly when a second tackifier or mutually compatible plasticizer is employed.

In particular embodiments, the plasticizer may be provided to the adhesive in amounts up to 90 weight percent, preferably less than 30 weight percent, and still more preferably less than about 15 weight percent of the adhesive. The plasticizer may be either a liquid or a solid at ambient temperature. Exemplary liquid plasticizers include hydrocarbon oils, polybutene, liquid tackifying resins, and liquid elastomers. Plasticizer oils are primarily hydrocarbon oils which are low in aromatic content and which are paraffinic or napthenic in character. Plasticizer oils are preferably low in volatility, transparent and have as little color and odor as possible. The use of plasticizers also may include the use of olefin oligomers, low molecular weight polymers, vegetable oils and their derivatives and similar plasticizing liquids.

When a solid plasticizing agent is employed, it may be desired that the agent have a softening point above 60° C. It is believed that by combining the homogeneous ethylene/α-olefin interpolymer with a suitable tackifying resin and a solid plasticizer such as a cyclohexane dimethanol dibenzoate plasticizer, the resulting adhesive composition may be applied at temperatures below 120° C., or even below 100° C. Although a 1,4-cyclohexane dimethanol dibenzoate compound commercially available from Velsicol under the trade name Benzoflex (Registered Trademark) 352 is exemplified, any solid plasticizer that will subsequently recrystallize in the compounded thermoplastic composition is suitable. Other plasticizers that may be suitable for this purpose are described in EP 0422 108 B1 and EP 0 410 412 B1, both assigned to H.B. Fuller Company.

Waxes may be usefully employed in suitable adhesive compositions, particularly when the adhesive composition is intended to be relatively tack free upon cooling and solidifying, such as for various packaging and bookbinding applications as well as foam in place gaskets. Waxes are commonly used to modify the viscosity and reduce tack at concentrations up to 60 percent by weight, or even less than about 25 percent by weight. Useful waxes may include paraffin waxes, microcrystalline waxes, Fischer-Tropsch, polyethylene and by-products of polyethylene wherein Mw is less than 3000. It may be desired that the concentration of wax be less than 35 percent by weight for high melt point waxes. At wax concentrations above 35 percent by weight, paraffin waxes may be used.

Also suitable are ultra-low molecular weight ethylene/α-olefin interpolymers prepared using a constrained geometry catalyst, and may be referred to as homogeneous waxes. Such homogeneous waxes, as well as processes for preparing such homogeneous waxes, are set forth in the Examples below. Homogeneous waxes, in contrast to paraffinic waxes and crystalline ethylene homopolymer or interpolymer waxes, will have a Mw/Mn of from 1.5 to 2.5, or even from 1.8 to 2.2.

Homogeneous waxes will be either ethylene homopolymers or interpolymers of ethylene and a C3-C20 α-olefin. The homogeneous wax will have a number average molecular weight less than 6000, or even less than 5000. Such homogeneous waxes may have a number average molecular weight of at least 800, or even at least 1300.

Homogeneous waxes lead to a low polymer and formulation viscosity, but are characterized by peak crystallization temperatures which are greater than the peak crystallization temperatures of corresponding higher molecular weight materials of the same density. In adhesive applications, the increase in peak crystallization temperature translates to an increased heat resistance, and the like, improved creep resistance in pressure sensitive adhesives, and improved SAFT in hot melt adhesives.

As is known in the art, various other components can be added to modify the tack, color, odor, etc., of a hot melt adhesive. Additives such as antioxidants (for example, hindered phenolics (for example, Irganox 1010, 565, and Irganox 1076), phosphites (for example, Irgafos 168)), anti-block additives, pigments, and fillers, can also be included in the formulations. It may be preferred that the additives should be relatively inert and have negligible effects upon the properties contributed by the homogeneous linear or substantially linear interpolymer, tackifying agent, and plasticizing oil.

Other potentially suitable adhesives including olefin polymers are described in U.S. Pat. No. 7,199,180, the disclosure of which is incorporated herein by reference in its entirety. Also suitable are tackifier-free adhesives, for example, such as those described in U.S. Ser. No. 13/836,385.

Additional examples of suitable adhesives are products designated H2861 and H20043F, products of Bostik S.A., Paris, France, and/or Bostik, Inc., Wauwatosa, Wis. Hot melt adhesives of a type deemed suitable for such use are typically mixtures of a high molecular weight polymer with lower molecular weight tackifiers and oils. A typical adhesive for this application might contain about 35% styrene-isoprene block copolymer with molecular weight of 80-250 kg/mol and 65% additives with molecular weights in the range of 0.5-3 kg/mol.

Low molecular weight species of, e.g., plasticizers included in some adhesives can be quite mobile at temperatures above the glass transition temperature of the mixture in which they reside. For example, in an adhesive formed of a mixture of components of the type contemplated herein, a high molecular weight polymer component may have a glass transition temperature Tg of, for example, about −50° C., while a lower molecular weight component may have a glass transition temperature Tg of, for example, about 80° C.; and the Tg for the mixture may be, for example, about 15° C. In such an example, the low molecular weight components can be relatively mobile at temperatures above 15° C. At room or body temperature, typical diffusion coefficients (The Mathematics of Diffusion, John Crank, Oxford University Press, USA ISBN-10: 0198534116) for these low molecular weight species in polymers like these are on the order of 10-13 m2/s.

As a consequence of this mobility, when these adhesives come into contact with a second material (e.g., an elastomeric film) the low molecular weight species can diffuse into the second material if they are soluble in the polymer(s) forming the second material. Conversely, if the second material contains low molecular weight species such as plasticizers, those may also diffuse into the adhesive, by the same mechanism. Without intending to be bound by theory, it is believed that either type of diffusion can decrease the apparent adhesion of the joint by two distinct mechanisms.

First, it may change the adhesive's composition. It is believed that this effect is more likely when elastomers with relatively high contents of oil are used. Diffusion of the oil into the adhesive material may cause unwanted plasticization of the end blocks of the adhesive polymer(s).

Second, the adhesive can lose mass if more material diffuses out than in, similar to the "moving marker" diffusion experiments known in the literature (see, for example, E. J. Kramer, P. Green and C. J. Palmstrom, Polymer (vol. 25, pp. 473-480) (1984). This effectively decreases the quantity of adhesive material present, which generally corresponds with decreased adhesion between the components joined.

Following experimentation, it is believed that replacing some of the elastomeric film's plasticizer with a tackifier as defined herein such as/or a tackifying resin as produced and sold by Eastman Chemical Company, Kingsport, Tenn. under the trademarks/trade names REGALREZ, REGALITE and EASTOTAC; Exxon Mobil Corp./ExxonMobil Chemical, Houston, Tex. under the trademark/trade name ESCOREZ; and Arakawa Europe GmbH, Schwalbach, Germany under the trademark/trade name ARKON, and the like, may address and reduce the effects of one or both mechanisms.

A suitable tackifier for this purpose may have a ring-and-ball softening point from 80° C. to 150° C., more preferably from 90° C. to 145° C., or even more preferably from 100° C. to 140° C.; a glass transition temperature Tg (midpoint) from 0° C. to 100° C., molecular weight Mn from 500 g/mol to 2000 g/mol.

While polyolefin-based adhesives may be suitable for the present invention, there may be other hot melt adhesives, such as styrenic-based adhesives, that can have a slow enough rate of crystallization such that the laminate may be harshly activated and not rupture and ultimately provide the extensibility described herein. In general, an adhesive may be suitable for the present invention if, during activation the adhesive is "open", that is, not yet fully, or even predominately, crystallized. In some embodiments, an adhesive may be suitable when its G'norm measured at 1 minute after the adhesive is applied to the nonwoven is at most about 0.2. In some embodiments, respectively, activation may occur before the adhesive achieves 95%, 90%, 85%, 80%, 75%, 70%, 65%, 60%, 55%, 50%, 45%, or 40% of its normalized modulus G' (G'norm).

While the particular adhesive used in the present invention has an important bearing whether the activation occurs at a time when the adhesive is not yet fully crystallized, it is to be understood that variables other than the particular adhesive may be such that the activation occurs before the adhesive is fully crystallized. For example, it is conceivable that the activation may occur so quickly after the adhesive is applied to the nonwoven that the same effect, that of activation occurring when the adhesive is not yet fully crystallized, may occur, and the laminate may be able to withstand the harsh activation and exhibit the increased extensibility. Or the adhesive may be heated up to a high temperature that slows the crystallization rate. The key is that the activation occurs during the open time before the adhesive achieves its full crystallization.

Figure 18:
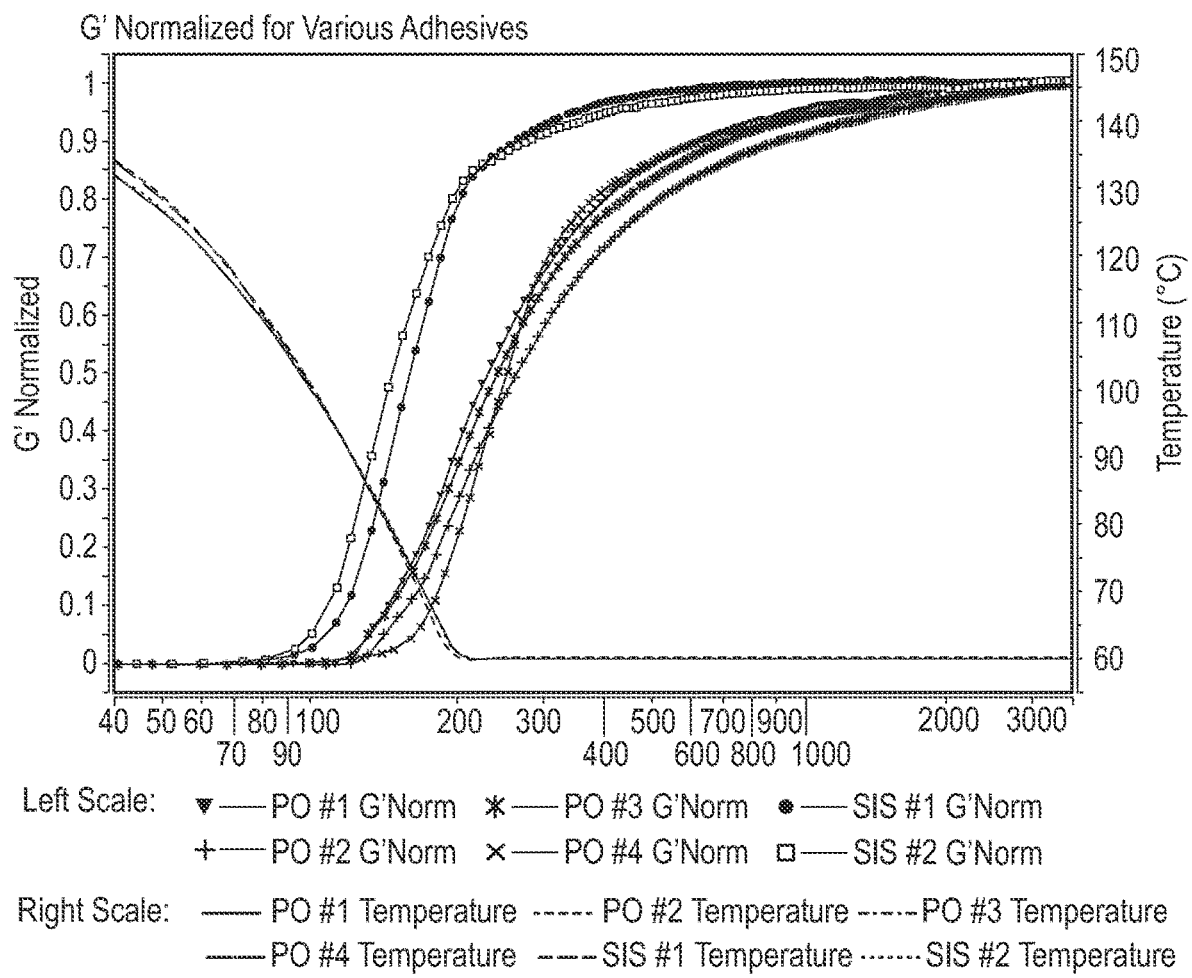
FIG. 18 is a graph of G'norm plotted as a function of time during the cooling step for two families of adhesives.

FIG. 18 is a graph of G'norm plotted as a function of time during the cooling step for two families of adhesives, polyolefins (PO) and styrenics (SIS). The graph demonstrates that, in general, polyolefins achieve crystallization more slowly than styrenics. As such, polyolefins may be exemplary adhesives for the present invention.

Nonwovens

Nonwoven webs of material, such as nonwoven fabric webs, may comprise sheets of individual nonwoven component layers bonded together using mechanical, thermal, or chemical bonding processes. Nonwoven webs may be formed as flat, porous sheets made directly from individual fibers, from molten plastic, and/or plastic film.

Continuous and discontinuous fiber spinning technologies of molten materials and typically of thermoplastics are commonly referred to as spunmelt technologies. Spunmelt technologies may comprise both the meltblowing process and spunbonding processes. A spunbonding process comprises supplying a molten polymer, which is then extruded under pressure through a large number of orifices in a plate known as a spinneret or die. The resulting continuous fibers are quenched and drawn by any of a number of methods, such as slot draw systems, attenuator guns, or Godet rolls, for example. In the spunlaying or spunbonding process, the continuous fibers are collected as a loose web upon a moving foraminous surface, such as a wire mesh conveyor belt, for example. When more than one spinneret is used in line for forming a multi-layered web, the subsequent nonwoven component layers are collected upon the uppermost surface of the previously formed nonwoven component layer.

The meltblowing process is related to the spunbonding process for forming a layer of a nonwoven material, wherein, a molten polymer is extruded under pressure through orifices in a spinneret or a die. High velocity gas impinges upon and attenuates the fibers as they exit the die. The energy of this step is such that the formed fibers are greatly reduced in diameter and are fractured so that microfibers of indeterminate length are produced. This differs from the spunbonding process where the continuity of the fibers are generally preserved. Often meltblown nonwoven structures are added to spunbond nonwoven structures to form spunbond, meltblown ("SM") webs or spunbond, meltblown, spunbond ("SMS") webs, which are strong webs with some barrier properties.

Suitable nonwoven web materials that may be useful in the present invention also include, but are not limited to spunbond, meltblown, spunmelt, solvent-spun, electrospun, carded, film fibrillated, melt-film fibrillated, air-laid, dry-laid, wet-laid staple fibers, and other and other nonwoven web materials formed in part or in whole of polymer fibers, as known in the art. The nonwoven web may be formed predominately of polymeric fibers. In some examples, suitable nonwoven fiber materials may include, but are not limited to polymeric materials such as polyolefins, polyesters, polyamide, or specifically, PET and PBT, polylactic acid (PLA), and alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers such as various types of Kraton), polystyrenes, polyamides, PHA (polyhydroxyalkanoates) and e.g. PHB (polyhydroxubutyrate), and starch-based compositions including thermoplastic starch, for example. The above polymers may be used as homopolymers, copolymers, e.g., copolymers of ethylene and propyelene, blends, and alloys thereof.

Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. Nos. 6,645,569, 6,863,933, and 7,112,621.

In the present invention, the outer layers may be of a nonwoven material, such as SM (spunbond meltblown), SMS (spunbond meltblown spunbond), and SMMS (spunbond meltblown meltblown spunbond), SSS (spunbond spunbond spunbond) nonwovens. A nonwoven may be called a spunbonded nonwoven even when it includes meltblown fibers.

In some embodiments, at least one of the nonwovens in the stretchable laminate is spunbonded. In some embodiments, both nonwovens are spunbonded. In some embodiments, one of the nonwovens may be carded.

In some embodiments, a nonwoven may comprise bicomponent fibers, in some embodiments, a nonwoven may be extensible. In some embodiments, a spunbonded nonwoven may have a basis weight of, respectively, at most 14 gsm, at most 15 gsm, at most 17 gsm, at most 19 gsm, or at most 21 gsm. In some embodiments, a carded nonwoven may have a basis weight of, respectively, at most about 24 gsm, at most 25 gsm, at most 27 gsm, at most 29 gsm, or at most 31 gsm.

Films

According to the present disclosure, the stretchable laminate comprises an elastic film between two nonwoven layers. Exemplary films may be elastomeric polymers. Non-limiting examples of elastomeric polymers include homopolymers, block copolymers, random copolymers, alternating copolymers, graft copolymers, and the like. Particularly suitable polymers for use in films exhibiting resistance to tear propagation are block copolymers, which are typically made of blocks (or segments) of distinct repeat units that each contribute to the properties of the polymer, such as those disclosed in U.S. patent application Ser. Nos. 13/026,533 and 13/673,277, respectively. One reason block copolymers are recognized as being useful, at least in part, is because the blocks of the copolymer are covalently bonded to one another and form microphase-separated structures with rubber domains that provide good extensability while the glassy end block domains provide mechanical integrity (e.g., good mechanical strength and avoidance of unwanted stress relaxation or flow). Block copolymers suitable for use herein may exhibit both elastomeric and thermoplastic characteristics. For example, the end-blocks may form domains that display stiff, rigid mechanical properties at temperatures that prevail during end use (e.g., 20° C.-40° C.), thereby adding rigidity and strength to the entire polymer. Such an end-block is sometimes referred to as a "hard block". The midblock may accommodate the relatively large deformations associated with elastomers and provides retractive force when the material is strained (i.e., stretched or extended). Such a midblock is sometimes referred to as a "soft block" or "rubbery block." Suitable block copolymers for use herein include at least one hard block (A) and at least one soft block (B). The block copolymers may have multiple blocks. In certain embodiments, the block copolymer may be an A-B-A triblock copolymer, an A-B-A-B tetrablock copolymer, or an A-B-A-B-A pentablock copolymer. Other suitable copolymers include triblock copolymers having endblocks A and A', wherein A and A' are derived from different compounds. In certain embodiments, the block copolymers may having more than one hard block and/or more than one soft block, wherein each hard block may be derived from the same or different monomers and each soft block may be derived from the same or different monomers.

Suitable hard block components have a glass transition temperature (Tg) greater than 25° C. or 45° C. or even 65° C., but typically less than 100° C. The hard block portion may be derived from vinyl monomers including vinyl arenes such as styrene and alpha-methyl-styrene or combinations thereof. The soft block portion may be a polymer derived from conjugated aliphatic diene monomers. Typically, the soft block monomers contain fewer than 6 carbon atoms. Suitable diene monomers such as, for example, butadiene and isoprene may be used as-polymerized or in their hydrogenated form. Suitable soft block polymers include poly(butadiene), poly(isoprene), and copolymers of ethylene/propylene, ethylene/butene, and the like. In certain embodiments, it may be desirable to partially or fully hydrogenate any residual olefinic double bonds contained in the copolymer or portion thereof (e.g., midblock or endblock).

In a particularly suitable embodiment, the elastomeric polymer may be a styrene-ethylene-ethylene-propylene-styrene ("SEEPS") block copolymer that includes two polystyrene endblocks of approximately 8 kg/mole each and a 45 kg/mole midblock. The midblock may be formed, for example, by copolymerizing and then hydrogenating isoprene and butadiene. It may be desirable to hydrogenate the copolymer such that from 95-99% or even 98-99% of the original C=C double bonds in the midblock are saturated but the polystyrene endblocks remain aromatically intact. If the degree of hydrogenation is too low, the polymer may begin to lose its ability to undergo strain-induced crystallization. It is believed, without being limited by theory, that strain induced crystallization in a polymer is important for providing tear resistant characteristics to films made with such polymers. In certain embodiments, copolymerizing isoprene and butadiene to produce the rubbery midblock may result in a copolymer that varies both in comonomer sequence and in vinyl content. While a SEEPS copolymer is a block copolymer, the ethylene-ethylene-propylene ("EEP") midblock is more of a random copolymer than blocky or alternating. But subtle departures from randomness may occur. The departures from randomness, as well as the vinyl content of the copolymer, may be controlled by adjusting the conditions during polymerization. For example, copolymerization of isoprene and butadiene with subsequent hydrogenation may give rise to a variety of branch types. Table 1 below exemplifies the different branch types that may result. With the partial exception of the methyl branches, the branches typically do not "fit" into the polyethylene-type crystals, and therefore decrease the midblock's degree of crystallinity and Tm. For example, the midblock of a SEEPS block copolymer may be approximately 7% crystalline at temperatures below −50° C. and have a Tm of approximately 0° C. In comparison, a substantially unbranched polyethylene is approximately 75% crystalline and has a Tm of approximately 135° C.

TABLE 1

| Isomer | Branch Type After Hydrogenation |
| --- | --- |
| 1,2 Isoprene | Methyl, Ethyl |
| 3,4 Isoprene | Isopropyl |
| 1,4 Isoprene | Methyl |
| 1,2 Butadiene | Ethyl |
| 1,4 Butadiene | No branch - possible to crystallize |

The length of the runs of crysallizable CH2 sequences, which directly impact the melting temperature of the polymer midblock, depends, at least partially, on the sequence of comonomer incorporation into the midblock (e.g., isoprene always gives a branch of some type) and the overall balance between 1,4 and 1,2 (or 3,4) polymerization of the dienes. The Tm of the crystal may provide information about the length of the crystallizable sequences and the ability of the material to undergo strain-induced crystallization, both of which are related to the number, type, and distribution of the branches on the midblock backbone. Suitable elastomers herein include sufficiently long crystallizable sequences of CH2 groups (which form polyethylene-type crystals) that have a Tm of greater than 10° C. (compared to, e.g., −5° C. for previously known materials). A suitable Tm for the elastomers herein is between 10° C. and 20° C., 12° C. and 18° C.; 13° C. and 17° C.; or even between 14° C. and 16° C.

In addition to the EEP midblocks described above, it may be desirable to provide a midblock of the "EB" type (i.e., hydrogenated polybutadiene) that contains similar crystallizable sequences, for example, by choosing the appropriate solvent polarity (which controls 1-4 vs. 1-2 content), as described in Anionic Polymerization: Principles and Practical Applications, Henry Hsieh, Roderick Quirk; Chapter 9, pp. 197-229; Marcel Decker, New York (1996).

Other exemplary elastomer films may include M18-1117 and M18-1361 elastomer film commercially available from Clopay Corporation of Cincinnati, Ohio and K11-815 and CEX-826 elastomer film commercially available from Tredegar Film Products of Richmond, Va. Such materials are believed to have good elasticity properties. Exemplary elastomer films may include those with coextruded "skin" layers, and those that are skinless.

In some embodiments, the elastic film of the laminate may be no thicker than, respectively, about 50 micrometers, about 60 micrometers, or about 70 micrometers.

Activation

Laminates of the present invention may be mechanically activated by one or a combination of activating means, including, activating the laminate through intermeshing gears or plates, activating the laminate through incremental stretching, activating the laminate by ring rolling, SELFing, activating the laminate by tenter frame stretching, and activating the laminate in the machine direction between nips or roll stacks operating at different speeds. Activation involves permanent mechanical displacement of fibers via rods, pins, buttons, structured screens or belts or other suitable technology. Suitable methods for activating and bonding the topsheet are disclosed in U.S. Publication No. 2010/0310837.

During the activation process, corrugated interengaging rolls are used to permanently elongate the substrate to reduce its resistance to stretch. The resulting laminate has a greater degree of stretchability in the portions that have been subjected to the activation, or ring rolling, process. Thus, this operation provides additional flexibility in achieving stretch properties in localized portions of the stretch composite. Methods for imparting stretchability to an extensible or otherwise substantially inelastic material by using corrugated interengaging rolls which incrementally stretch in the machine (MD) or the cross-machine direction (CD) and permanently deform the material are disclosed in U.S. Pat. Nos. 4,116,892; 4,834,741; 5,143,679; 5,156,793; 5,167,897; 5,422,172; and 5,518,801.

Incremental stretching rollers may be used to activate laminates in the MD, CD, at an angle, or any combination thereof. In some embodiments, the depth of engagement used for incremental stretching is about 0.05 inches, about 0.10 inches, about 0.15 inches, about 0.20 inches, or about 0.25 inches. The depth of engagement can be, for example, at least about 0.05 inches or at least about 0.10 inches. The depth of engagement can be, for example, no more than about 0.10 inches, no more than about 0.18 inches, or no more than about 0.25 inches. The pitch (i.e. tooth spacing on one roll) of the ring rolls can range from 1.5 mm to about 5 mm.

TABLE 2

| DOE (in.) | DOE (mm) | DOE/ Pitch150 | eng strain on 150p | strain rate for 275mpm |
| --- | --- | --- | --- | --- |
| 0.05 | 1.27 | 0.33 | 0.21 | 156 |
| 0.1 | 2.54 | 0.67 | 0.73 | 377 |
| 0.15 | 3.81 | 1.00 | 1.37 | 595 |
| 0.2 | 5.08 | 1.33 | 2.05 | 784 |
| 0.25 | 6.35 | 1.67 | 2.76 | 956 |
| 0.3 | 7.62 | 2.00 | 3.48 | 1109 |

In some embodiments, the depth of engagement used for incremental stretching is about 0.05 inches, about 0.10 inches, about 0.15 inches, about 0.20 inches, or about 0.25 inches. In some embodiments, the depth of engagement (as a fraction of ring roll pitch) used for incremental stretching is about 0.33, to 2.0 (see table 2 above.)

The depth of engagement can be, for example, at least about 0.05 inches or at least about 0.10 inches. The depth of engagement can be, for example, no more than about 0.10 inches, no more than about 0.18 inches, or no more than about 0.25 inches. The depth of engagement (as a proportion of pitch) is set based on desired amount of stretch, while avoiding unwanted holes in the laminate's film. The useful range is 1-2.

The pitch of engagement can be, for example, from about 0.060 inches to about 0.200 inches, from about 0.080 inches to about 0.150 inches, or from about 0.100 inches to about 0.125 inches. Further, laminates may be activated at the high strain rates that correspond to the commercially useful line speeds, via, for example, the ring rolling activation process. The activation may occur immediately after the lamination process or may occur as the laminate is unwound from a roll on which it was stored.

Figure 15:
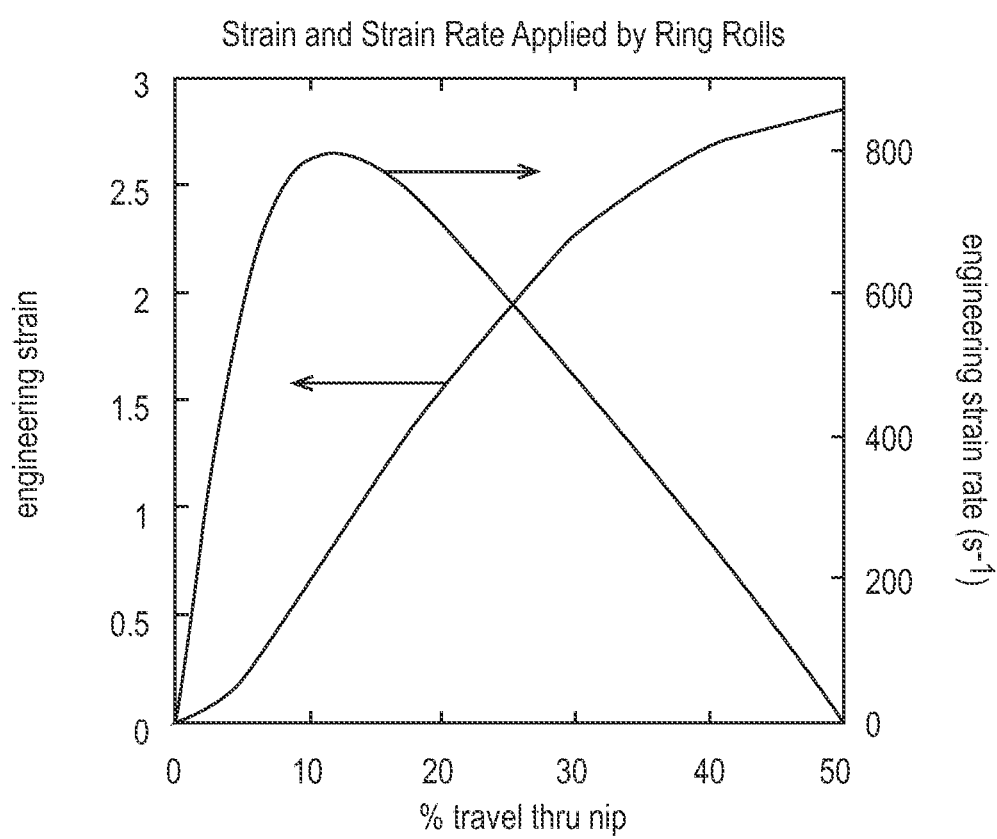
FIG. 15 is a graph of the strain and strain rate applied by ring rolls during activation.

The material undergoes transverse direction strain as it passes through the intedigitating ring roll teeth. The amount of strain is determined by the DOE, pitch, and shape of tooth tip. As shown in FIG. 15, the strain rate increases to a maximum, then gradually decreases to zero as the material approaches the center of the nip.

In some embodiments, the activation may be achieved by ring rolls that impose tensile deformation on the spans of material between ring roll teeth. The amount of deformation may be expressed as an engineering strain $e=(1-l\_0)/l\_0$ where l0 and l are the length of the material span before and after deformation respectively. (Materials Science and Engineering: An Introduction, 8th Edition by William D. Callister, David G. Rethwisch ISBN 978-0-470-41997-7).

In some embodiments, respectively, the minimum applied strain may be 150%, 180%, 210%, 240%, 250%, 260%, 270%, 280%, 290%, 300%, 310%, 320%, 325%, 330%, 340%, 350%, 400%, or 450%. In some embodiments, the minimum strain rate at which the strain is imposed, $de/dt=s/l\_0$, where s at which one end of the span moves with respect to the other end, may be, respectively, about 700/sec, 750/sec, 800/sec, 850/sec, 900/sec, 950/sec, 1000/sec, 1050/sec, 1100/sec, 1200/sec, 1300/sec, 1400/sec, 1500/sec, 1600/sec, 1700/sec, 1800/sec, 1900/sec, or 2000/sec. In some embodiments, the maximum strain rate (as shown in plot) may be about 500 s-1 on the low end and 2000 s-1 on the high end, and in some other embodiments 2000/sec. Because deformation might not always be homogeneously distributed throughout the span of material, local strain rates in the span may surpass 1500/sec or more in some locations.

These speed considerations are important because film rupture occurs as a result of transfer of strain energy between film and nonwoven, and the material properties that determine how the layers in the material interact mechanically with one another (modulus, yield strength, and fracture toughness) vary strongly with deformation rate. The higher the deformation rate the higher the modulus of the nonwoven material and the more localized the strain, which intensifies the local transfer of strain energy into the film.

FIG. 1, is a schematic illustration of an apparatus suitable for use in the method of the present invention for activation of the laminate. The apparatus and method provide a physically modified web or laminate having improved physical properties and which can then be further processed, alone or together, with other materials without the laminate experiencing disintegration, rupture, or loss of integrity. As used herein, the word "web" is intended to encompass continuous rolls and discrete sheets of the materials, though the web in a continuous form is more suitable for high-speed production purposes.

The web has a longitudinal axis that extends along the web movement or "machine" (MD) direction of the web, and a transverse axis that extends in the cross-web or "cross-machine" (CD) direction of the web.

Referring again to FIG. 1, web 5 is withdrawn from supply roll 4 and travels in the direction indicated by the arrow. Alternatively, web 5 is formed directly off an extruder equipped with a film die, and optionally a set of tension or take-up rolls between the extruder and forming station 6. Web 5 is fed to the nip 7 formed by a pair of opposed forming rolls 8 and 9 that together define a first forming station 6. The structure and relative positions of forming rolls 8, 9 are shown in an enlarged perspective view in FIG. 2. As shown, rolls 8 and 9 are carried on respective rotatable shafts 21, 23, having their axes of rotation disposed in parallel relationship. Each of rolls 8 and 9 includes a plurality of axially-spaced, side-by-side, circumferentially-extending, equally-configured teeth 22 that can be in the form of thin fins of substantially rectangular cross section, or they can have a triangular or an inverted V-shape when viewed in cross section. If they are triangular, the vertices of teeth 22 are outermost. In any event, the outermost tips of the teeth are preferably rounded, as shown in greater detail in FIGS. 3 and 4, to avoid cuts or tears in the materials, such as web 5, that pass between the rolls.

The spaces between adjacent teeth 22 define recessed, circumferentially-extending, equally configured grooves 24. The grooves can be of substantially rectangular cross section when the teeth are of substantially rectangular cross section, and they can be of inverted triangular cross section when the teeth are of triangular cross section. Thus, each of forming rolls 8 and 9 includes a plurality of spaced teeth 22 and alternating grooves 24 between each pair of adjacent teeth. The teeth and the grooves need not each be of the same width, however, and preferably the grooves have a larger width than that of the teeth, to permit the material that passes between the interengaged rolls to be received within the respective grooves and to be locally stretched, as will be explained hereinafter.

Figure 3:
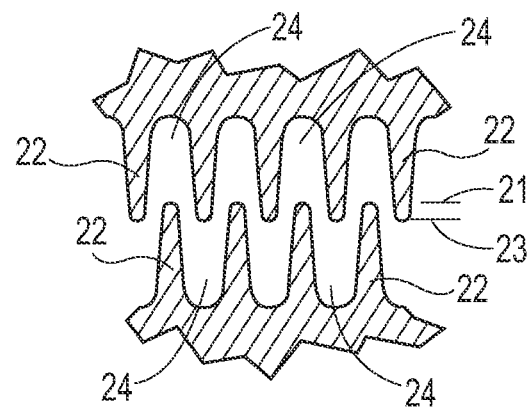
FIG. 3 is an enlarged, fragmentary, cross-sectional view showing the interengagement of respective teeth and grooves of the forming rolls shown in FIG. 2.

FIG. 3 is an enlarged, fragmentary, cross-sectional view showing the interengagement of teeth 22 and grooves 24 of the respective rolls. As shown, generally triangular teeth 22 of one roll extend partially into generally triangular grooves 24 of the opposed roll, so that imaginary lines 21 and 23 interconnecting the rounded outer tips of teeth 22 of rolls 8 and 9, respectively, lie radially inwardly of the rounded outer tips of teeth 22 of the opposed roll. The respective axes of rotation of rolls 8 and 9 so spaced from each other that there is a predetermined space or gap between the opposed sidewalls of the interengaged teeth and grooves of the respective rolls.

Figure 4:
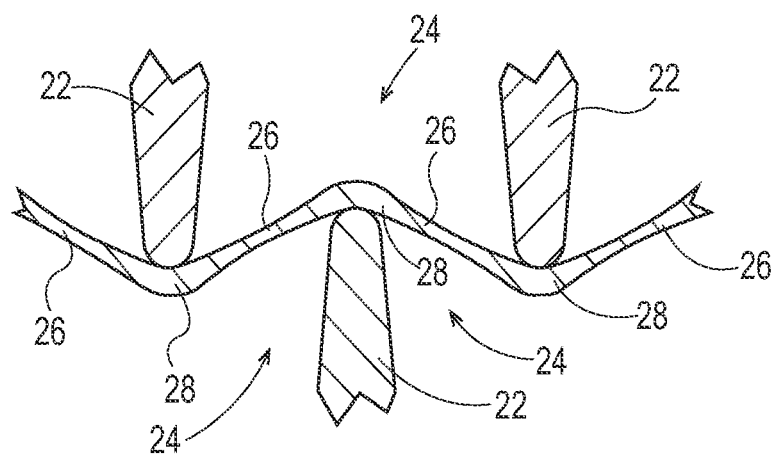
FIG. 4 is a further enlarged, fragmentary, cross-sectional view showing the tip portions of the interengaged forming roll teeth with a web of material positioned between the rolls and spanning and in contact with the tips of adjacent teeth.

FIG. 4 is an even further enlarged view of several interengaged teeth 22 and grooves 24 with a web of material being modified therebetween. As shown, a portion of web 20, which is the modified material of the precursor web 5 of FIG. 1, is received between the interengaged teeth and grooves of the respective rolls. The interengagement of the teeth and grooves of the rolls causes laterally spaced portions of web 20 to be pressed by teeth 22 into opposed grooves 24. In the course of passing between the forming rolls, the forces of teeth 22 pressing web 20 into opposed grooves 24 impose within web 20 tensile stresses that act in the cross-web direction. The tensile stresses cause intermediate web sections 26 that lie between and that span the spaces between the tips 28 of adjacent teeth 22 to stretch or extend in a cross-web direction, which results in a localized reduction of the web thickness at each of intermediate web sections 26.

In one embodiment, there is a substantially uniform distribution of local strain over the span between adjacent teeth. The portions of web 20 that lie between the adjacent teeth are locally stretched while the portions of the web that are in contact the tips of the teeth typically do not undergo a similar degree of extension. Not intending to be bound by theory, it is believed that the frictional forces exist between the surfaces at the rounded outer ends (i.e., tips) of teeth 22 and the adjacent surfaces 28 of web 20 that are in contact therewith. The frictional forces reduce the sliding movement of those portions of the web surfaces relative to the tooth tip surfaces. Consequently, the thickness of web portion 28 that are in contact with the tooth tips reduces only slightly, as compared with the web thickness reductions that occur at intermediate web portion 26.

Figure 5:
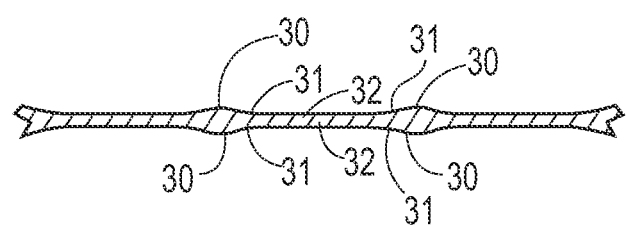
FIG. 5 is an enlarged, fragmentary, cross-sectional view taken along the cross-web direction of a web of material that has passed through a pair of forming rolls such as those shown in FIG. 2.

However, in a typical process according to the present invention, there is a nonuniform distribution of the local strains over the span between adjacent teeth. FIG. 5 illustrates the modified web having a drawn portion 32 which has been fully drawn (i.e., drawn to the natural draw ratio of the material), an unstretched portion 30 and an intermediate portion 31. When material is substantially fully drawn in a web portion 32, no further deformation takes place and no more open areas are being formed. Thus, the micropores and capillaries are "stabilized" or "fixed". The area where the web material are being stretched are primarily in the intermediate portion 31. In the local (i.e., between adjacent web portions 30, 31 and 32) stretching process, the web material in the unstretched portion 30 are being incorporated into the intermediate portion 31 where the deformation takes place. The intermediate portion 31 is typically referred to as the "neck" region. As used herein, the term "neck" refers to the constriction in at least one dimension by applying a tension force in a direction perpendicular to the desired direction of constriction (which is sometimes called a "neck down").

The action of pressing of portions of web 20 into the respective grooves 24 by teeth 22 therefore causes a nonuniform reduction of the thickness of web 20 to take place in the cross-web direction of the web. Accordingly, web 20 undergoes a greater reduction in thickness in the cross-web portions of the web that extend between and that span adjacent teeth 22 than it undergoes at those cross-web portions of the web that are in contact with the surfaces at the outer ends of teeth 22. Thus, by virtue of passing through the interengaged rolls and being locally laterally stretched at spaced intervals between adjacent teeth, the upper and lower surfaces of the web after it passes from between the opposed rolls define modulating surfaces that are the mirror images of each other when the web is viewed in cross section in the cross-web direction, as shown in FIG. 5. Modulating upper and lower surfaces of the web include alternating peaks 30 and valleys 32, which define alternating heavy and light basis weight regions. The light basis weight regions are found at the positions of the web wherein the web material has been locally laterally stretched. The localized stretching of the web in the cross-web direction results in a wider (as manifested in the increase in the surface contour length) modified web that has a plurality of spaced, longitudinally-extending, localized areas of reduced web thickness. Additional cross-web stretching of the exiting, formed web can be effected by passing the modified web between so-called Mount Hope rolls, tentering frames, angled idlers, angled nips, and the like (not shown), each of which is known to those skilled in the art.

Because of the localized cross-web stretching of web 5 that has taken place, with the consequent increase in web width, the modified web 20 that exits from the forming rolls at first forming station 6 has a lower basis weight than that of the entering precursor web 5, provided the exiting material remains in a substantially flat, laterally extended state. The laterally-stretched web as it exits from between the forming rolls may contract laterally to its original width. When the web is placed under some tension in the web movement direction, the exiting, modified web may have the same basis weight as it had in its entering condition. If the exiting modified web is subjected to a sufficiently high web movement direction tension, the exiting modified web can be made to contract to a smaller width than its original width, in which case the web will have a greater basis weight than its original basis weight. On the other hand, if the web is subjected to sufficient additional cross-web stretching by passing the modified web between so-called Mount Hope rolls, tentering frames, angled idlers, angled nips, or the like as described above, the exiting, modified web will have less than its original basis weight. Thus, by selecting a suitable forming roll tooth and groove configuration, by selecting a suitable web movement direction tension level, and by selecting whether or not to subject the web to additional cross-web stretching, the resulting modified web can have a web width that can range from about 25% to about 300% of the unmodified, precursor web width and a basis weight that is less than, equal to, or greater than the unmodified, precursor web's original basis weight.

Teeth 22 and grooves 24 can be generally triangular in cross section, as shown in FIG. 3, and preferably each of teeth 22 is of the same size so that each of the opposed teeth and grooves on respective forming rolls 8, 9 interengage with each other along the entire axial lengths of each of the rolls. In one embodiment, teeth having a peak-to-peak pitch of the order of about 0.030 to 0.100 inches, having sidewalls disposed at an included angle of the order of about 90 to 120, and having a tip-to-base tooth height and groove depth of the order of about 0.060 to 0.300 inches can be employed in carrying out the present invention. As will be appreciated by those skilled in the art, the sizes of the respective teeth and grooves can be varied within a wide range and would still be effective to carry out the present invention. In that regard, additional structural details of suitable forming rolls are provided in U.S. Pat. No. 5,156,793, entitled "Method for Incrementally Stretching Zero Strain Stretch Laminate Sheet in a Non-Uniform Manner to Impart a Varying Degree of Elasticity Thereto," which issued on Oct. 20, 1992, to Kenneth B. Buell et al.; in U.S. Pat. No. 5,167,897 entitled "Method for Incrementally Stretching a Zero Strain Stretch Laminate Sheet to Impart Elasticity Thereto," which issued on Dec. 1, 1992, to Gerald M. Webber et al.; and in U.S. Pat. No. 5,518,801, entitled "Sheet Materials Exhibiting Elastic-Like Behavior," which issued on May 21, 1996, to Charles W. Chappell et al., the disclosures of each of which patents are hereby incorporated by reference herein.

If the web is expanded only in the X-Y plane, there will be a substantial decrease in the basis weight of the modified web, which serves to reduce the cost of any components of which the modified web is a part. Preferably, the width of the modified web of the present invention is about 100% greater than the original width of the unmodified, precursor web. On the other hand, if the web movement direction (MD) tension on the modified web as it exits the forming rolls is sufficiently high, the modified web will have a width that is less than its original width, and a greater basis weight than that of the unmodified, precursor web.

Figure 6:
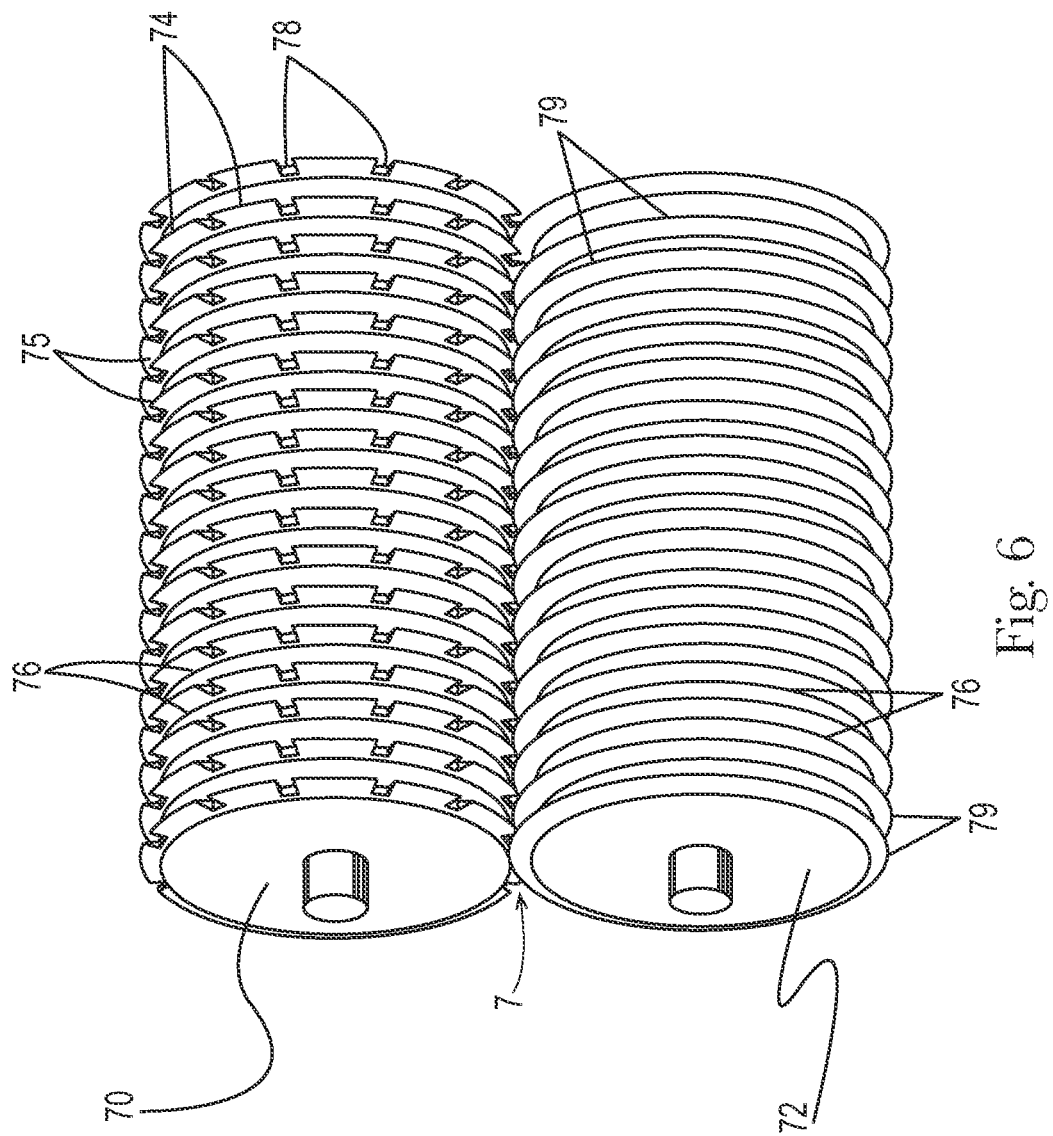
FIG. 6 is a fragmentary perspective view of a pair of closely-spaced forming rolls having tooth and groove configuration on the surface wherein one roll has notched teeth and the other roll has unnotched teeth.

FIG. 6 shows another configuration of opposed forming rolls, which can be used to expand portions of the web in the web thickness dimension, that is, by expanding portions of the web out of the X-Y plane into the Z-direction. As shown in FIG. 1, an unmodified web 5 is fed from a supply roll 4 into the nip 7 of opposed forming rolls 70 and 72 which define forming station 6. Roll 70 includes a plurality of circumferentially-extending, axially-spaced circumferential teeth 75. However, unlike continuous circumferential teeth 22 of forming roll 8 shown in FIG. 2, circumferential teeth 75 of roll 70 include a plurality of circumferentially-spaced ridges 74, and intervening circumferentially-spaced notched regions 78 that define recessed, open regions on teeth 75. As shown in FIG. 6, notches 78 on respective axially adjacent circumferential teeth 75 are aligned laterally to define a plurality of circumferentially-spaced groups of notched regions 78 about the periphery of roll 70. The respective laterally-extending groups of notched regions each extend parallel to the axis of roll 70.

Figure 2:
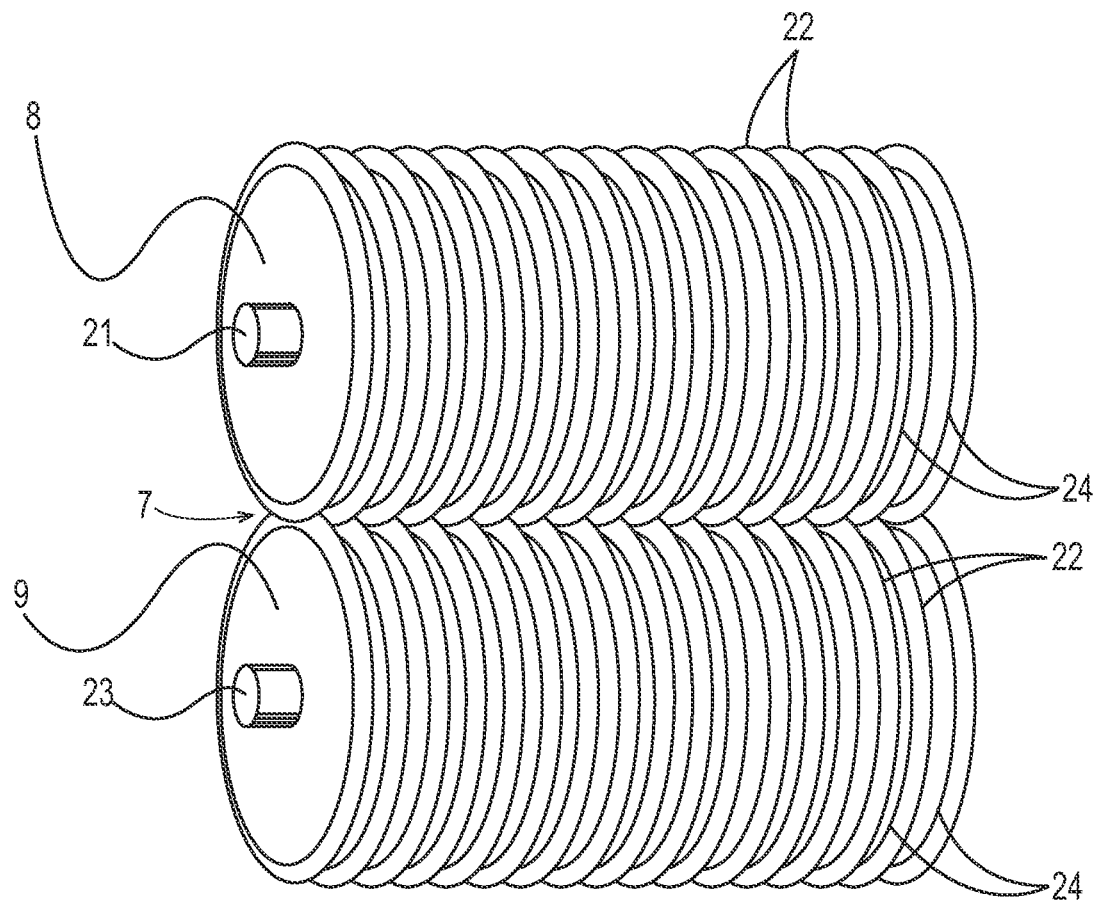
FIG. 2 is a fragmentary perspective view of a pair of closely-spaced forming rolls each having alternating and interengaging peripheral teeth and grooves.

Roll 72 is similar in overall construction to forming rolls 8 and 9 as shown in FIG. 2 in that roll 72 includes a plurality of circumferentially-extending, axially-spaced teeth 79 that extend in continuous, uninterrupted form about the circumference of the roll. Teeth 79 of roll 72 intermesh with teeth 75 of roll 70. But the portion of the web that passes between the notched regions 78 of roll 70 and the teeth 79 of roll 72 will be unformed, i.e., the web will not be deformed or stretched in that area and will remain substantially planar, while the portions of the web passing between ridges 74 of roll 70 and the teeth 79 of roll 72 will be deformed or stretched beyond the elastic limit of the web, resulting in a plurality of raised, rib-like elements. The raised, rib-like elements on the modified web provides a cloth-like texture, which improves the comfort and feel of the absorbent article containing such cloth-like, texturized web.

Figure 7:
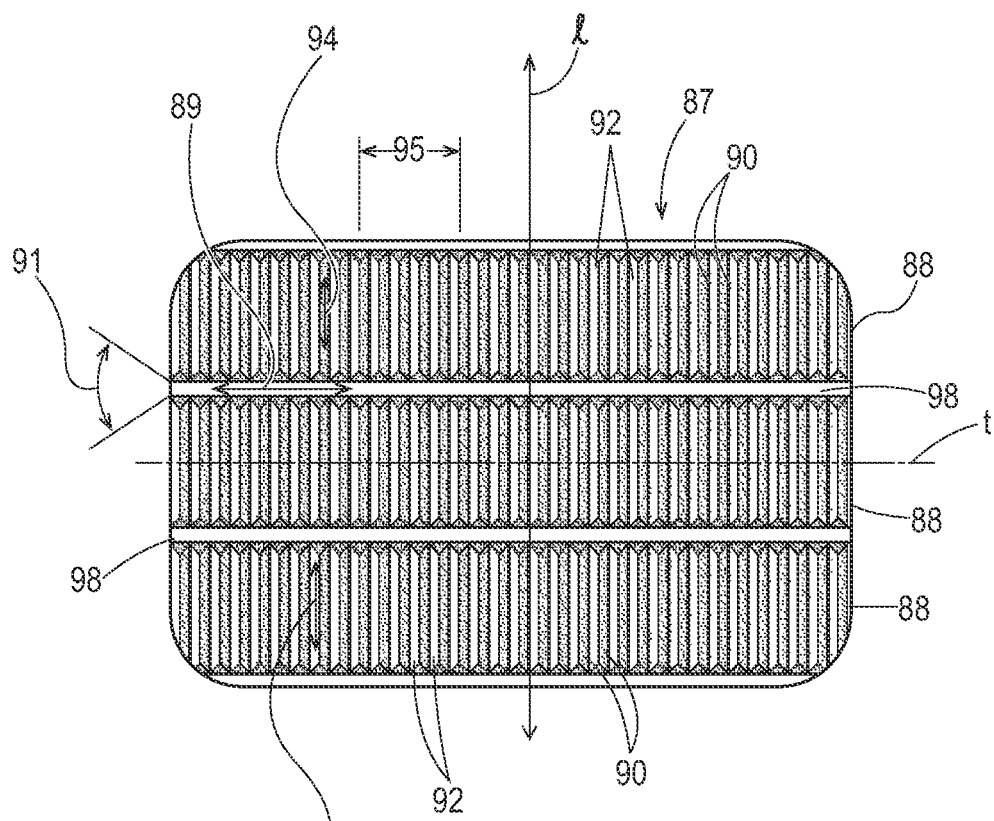
FIG. 7 is a top plan view of web material after it has passed between forming rolls having the teeth structure as shown in FIG. 6.
Figure 8:
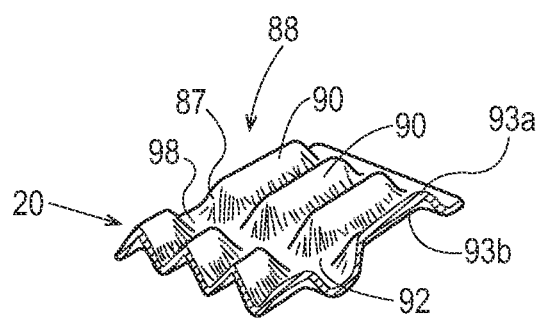
FIG. 8 is an enlarged fragmentary perspective view of a portion of the web shown in FIG. 7.

The forming rolls suitable for use herein to provide z-direction expansion in the modified web may have various tooth and groove configurations on the surface of the forming rolls. Typically, the teeth are spaced, circumferentially extending ridges (FIG. 2). The teeth may have circumferentially spaced notches in the ridges, producing spaced, rectangular arrays of raised ribs in the z-direction in the resulting modified web (FIGS. 7 and 8). More detailed descriptions and illustrations of the texturizing/forming rolls can be found in U.S. Pat. No. 5,518,801, issued May 21, 1996 to Chappell et al.; U.S. Pat. No. 5,650,214, issued on Jul. 22, 1997 to B. J. Anderson et al.; the disclosures of which are hereby incorporated by reference.

Referring now to FIGS. 7 and 8, there is shown a portion of a modified web 20 which has passed between a pair of opposed, interengaged forming rolls 70 and 72 having the tooth configurations shown in FIG. 6. Web 20 has two centerlines, a longitudinal centerline, which is also referred to hereinafter as an axis, line, or direction "l" and a transverse or lateral centerline, which is also referred to hereinafter as an axis, line, or direction "t". The transverse centerline "t" is generally perpendicular to the longitudinal centerline "l".

Web 20 includes a network of distinct regions. The network includes at least a first region 98, a second region 92, and a transitional region 87, which is at the interface between the first region 98 and the second region 88. Web 20 also has a first surface 93a and an apposite-facing second surface 93b. In the embodiment shown in FIGS. 7 and 8, web 20 includes a plurality of substantially flat, longitudinally spaced first regions 98 and a plurality of alternating second regions 88.

First regions 98 have a first, transversely-extending axis 89 and a second, longitudinally-extending axis 91, wherein the first axis 89 is preferably longer than the second axis 91. The first axis 89 of the first region 98 is substantially parallel to the transverse axis of web 20, while the second axis 91 is substantially parallel to the longitudinal axis of the web.

Second regions 88 have a first, transversely-extending axis 95 and a second, longitudinally-extending axis 94. The first axis 95 is substantially parallel to the transverse axis of the web, while the second axis 94 is substantially parallel to the longitudinal axis of the web. In the preferred embodiment of FIGS. 7 and 8, the first regions 98 and the second regions 88 are substantially linear, each extending continuously in a direction substantially parallel to the longitudinal axis of the web.

In the embodiment shown in FIGS. 7 and 8, first regions 98 are substantially planar. That is, the material within first regions 98 is substantially flat and is in substantially the same condition after the modification step undergone by web 20 by passage between interengaged rolls 70 and 72 shown in FIG. 6 as it was in before the web was passed between the forming rolls.

Second regions 88 include a plurality of raised, rib-like elements 90 that have a first or major axis 94 that is substantially parallel to the longitudinal axis of the web 20, and a second or minor axis 95 that is substantially parallel to the transverse axis of web 20. The dimension of rib-like elements 90 along first axis 94 is at least equal to, and preferably longer than, the dimension along second axis 95. Preferably, the ratio of the dimension of rib-like elements 90 along first axis 94 to the dimension along second axis 95 is at least 1:1, and more preferably at least 2:1 or greater. Further, rib-like elements 90 in second region 92 are adjacent one another and are separated from each other by an unformed area 98 having a width in the direction perpendicular to the major axis 94 of the rib-like elements. The dimensions of the rib-like elements can also be varied, if desired. A more detailed description of a web having first and second regions as shown in FIGS. 7 and 8 is provided in U.S. Pat. No. 5,518,801, the disclosure of which has already been incorporated herein by reference.

Figure 11:
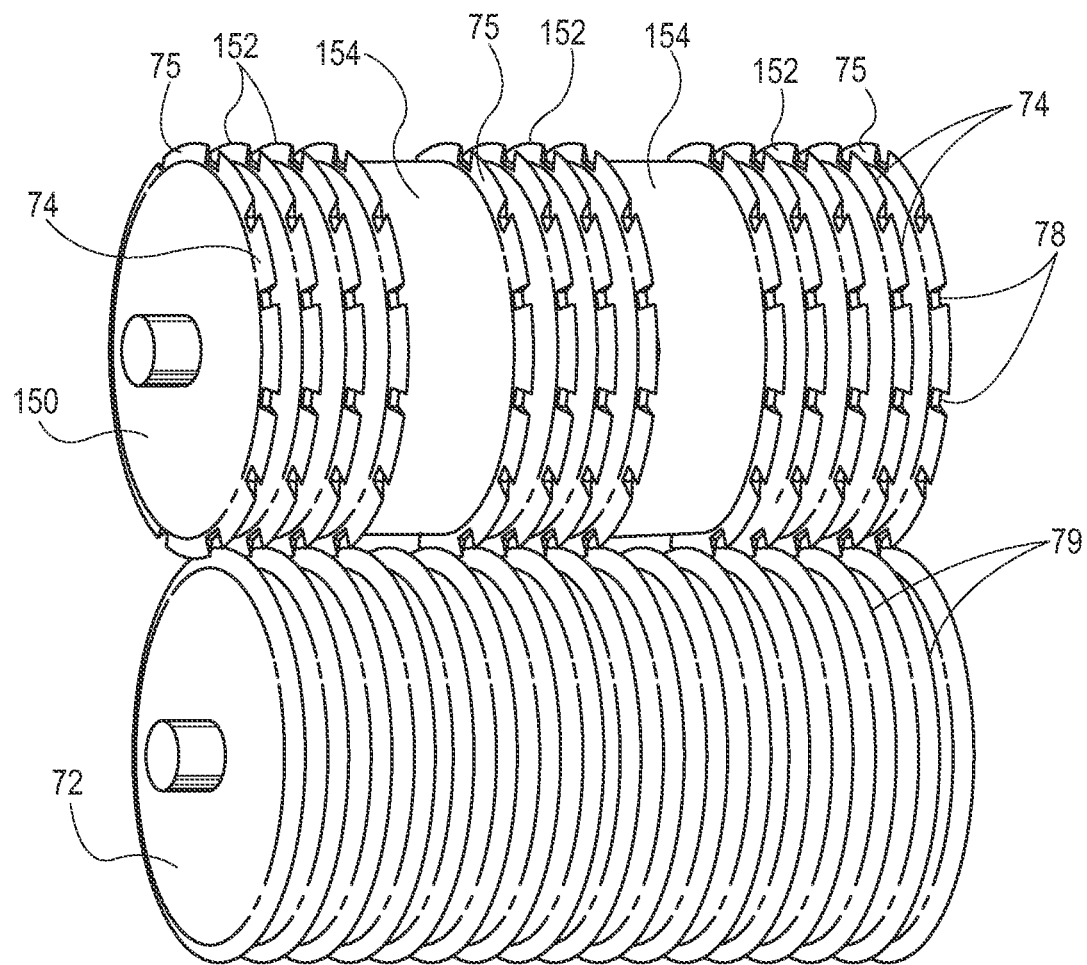
FIG. 11 is an enlarged, fragmentary perspective view of another set of forming rolls wherein the upper roll has interrupted teeth and groove configuration having notched teeth, and the lower roll has uninterrupted teeth.

Other arrangements of the teeth and grooves on the forming rolls known to those skilled in the art are also contemplated by the present invention. For example, the teeth may be arrangement in groups of rectangular arrays, wherein each group has several teeth and the respective groups of teeth are separated by an intervening gap that is devoid of teeth (FIG. 11). Additionally, the forming rolls may have decorative shapes, either as protruding teeth or as recessing grooves, on the roll surface. Nonlimiting examples of the decorative shapes include geometric shapes, animal shapes, floral or botanical shapes, cartoon figures.

Figure 9:
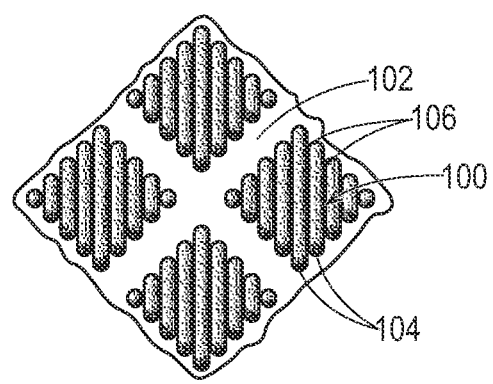
FIG. 9 is an enlarged fragmentary view of a portion of the modified web surface after the web has passed between a set of forming rolls having alternating teeth and grooves that define a diamond-like pattern.

In addition to the surface patterns illustrated in FIGS. 7 and 8 in the form of ridges and grooves, all of substantially equal lengths to define generally rectangular areas of deformation, the desired stretching or thinning of a web can, if desired, be effected by other forming roll tooth and groove configurations that can cause localized stretching of the material. For example, as shown in FIG. 9, instead of spaced rectangular arrays of ridges and grooves the deformation pattern can be in the form of ridges and grooves defining an array of spaced, diamond-shaped elements 100 with intervening undeformed areas 102. Each such diamond-shaped element is defined by alternating rib-like elements 106 and intervening grooves 104. Examples of methods and apparatus for formation of such diamond-shaped elements are disclosed in U.S. Pat. No. 5,650,214, entitled, "Sheet Materials Exhibiting Elastic-Like Behavior and Soft, Cloth-Like Texture", which issued on Jul. 22, 1997, to Barry J. Anderson, et al., the disclosure of which is incorporated herein by reference.

Figure 10:
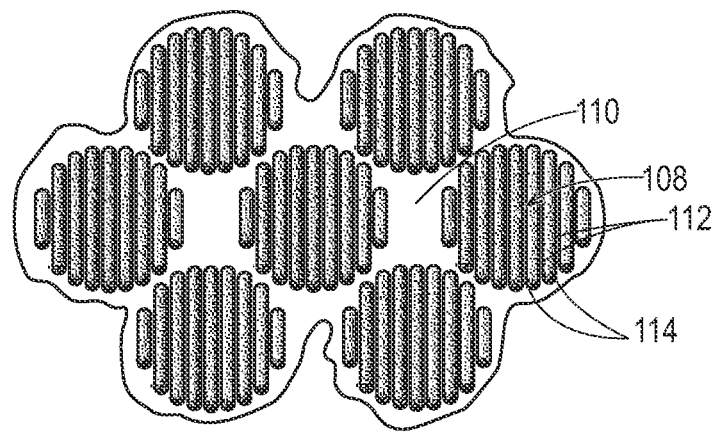
FIG. 10 is a fragmentary perspective view of a modified web surface, illustrating another forming roll tooth and groove pattern.

As shown in FIG. 10, the deformation pattern can also be in the form of ridges and grooves that together define an array of spaced, circularly-shaped elements 108. Each such circular element can be defined by varying-length rib-like elements 114 and intervening grooves 112. Between respective circularly-shaped elements 108 are unformed intervening areas 110. As will be apparent to those skilled in the art, other deformation patterns can also be employed, if desired, such as those illustrated and described in U.S. Pat. No. 5,518,801, the disclosure of which was earlier incorporated herein by reference.

Another set of forming rolls, having a different arrangement of the peripheral teeth and grooves and that can be utilized in the practice of the present invention, is shown in FIG. 11. Forming roll 150 is similar to forming roll 70 shown in FIG. 6 except that the circumferentially-extending teeth 75 are provided in respective groups 152, each group containing several teeth 75. Each of groups 152 of teeth 75 is spaced from an adjacent group of teeth in the axial direction of the roll, and the respective groups of teeth are separated by an intervening gap 154 that is devoid of teeth. Forming roll 72 of FIG. 11 has the same configuration as forming roll 72 of FIG. 6.

Because of the general structural similarity of the teeth and grooves on the several forming rolls shown in FIGS. 2, 6, and 11, the same reference numerals have been applied to corresponding parts of the rolls shown in FIGS. 2, 6, and 11.

Figure 12:
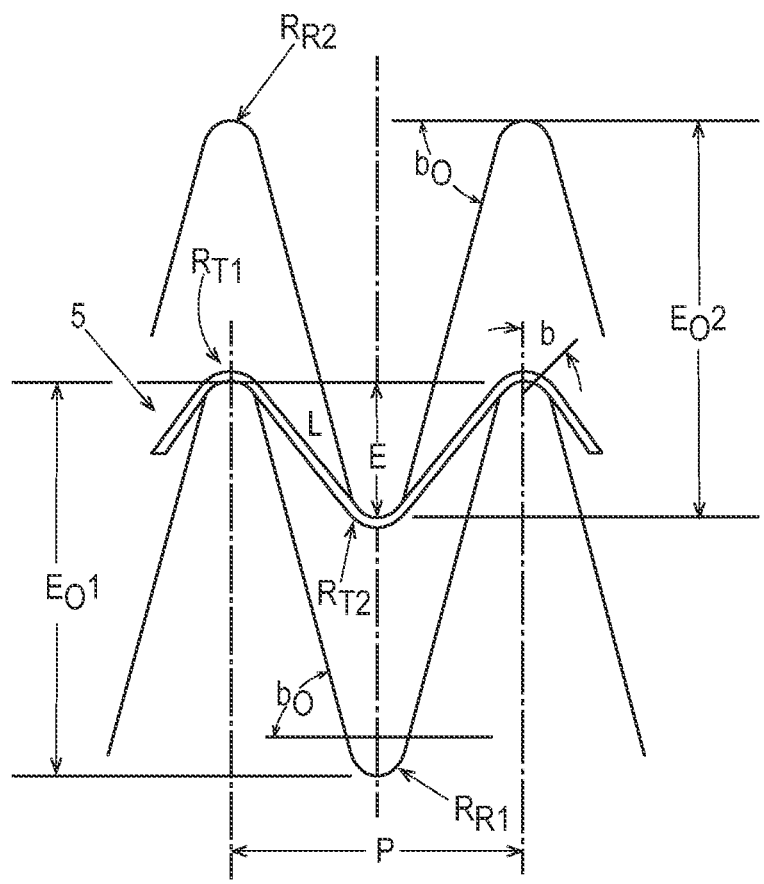
FIG. 12 is a schematic illustration of the tooling and operating parameters that contribute to the engineering strain rate.

Another useful process parameter is the engineering strain rate as calculated below. In a modification process according to the present invention, a precursor web passes between at least one pair of interengaging rolls where the teeth on the roll surface stretch the web incrementally. FIG. 12 shows a representative geometry for teeth on two interengaging rolls, wherein RT1 and RT2 are the tip radii of the teeth profiles, P is the tooth pitch, and E is the depth of engagement.

The engagement depth E is a function of time:

$$E(t) := E - Di \cdot \left[1 - \cos\left[\left[\frac{t}{(2 \cdot T)}\right] \cdot \left(2 \cdot \text{acos}\left(1 - \frac{E}{Di}\right)\right) - \text{acos}\left(1 - \frac{E}{Di}\right)\right]\right].$$

wherein Di is the roll diameter, and t has a value ranging from zero (at the initiation of engagement) to T (at total engagement or just prior to the initiation of disengagement). T can be calculated as below:

$$T := \text{acos}\left(1 - \frac{E}{Di}\right) \cdot \frac{Di}{2 \cdot Vw}.$$

The average local strain, Strain(t), is dependent on the pitch P, the length between the tangent of the tooth tips L(t) and the wrap length on tooth tips S(t):

$$L(t) := [(E(t) - RT1 - RT2)^2 + (0.5 \cdot P)^2 - (RT1 + RT2)^2]^{0.5}.$$

$$S(t) := (RT1 + RT2)\left[3.14159 - \text{atan}\left[0.5 \frac{P}{(E(t) - RT1 - RT2)}\right] - \text{acos}\left[\frac{(RT1 + RT2)}{[(E(t) - RT1 - RT2)^2 + (0.5P)^2]^{0.5}}\right]\right].$$

-continued
$$\text{Strain}(t) := \left[\frac{2 \cdot (L(t) + S(t))}{P} - 1\right] \cdot 100.$$

The average local strain rate can be calculated by taking the derivative of the average local strain, and the engineering strain rate is calculated by setting the second derivative of the average local strain to zero (i.e., the maximum of the average local strain rate versus time curve). As shown above, the engineering strain rate is a function of several tooling and operating variables, including roll diameter, tooling pitch (which determines the span between neighboring teeth), depth of engagement of the teeth, roll diameter, web speed (which determines the engagement speed), and tooth tip radius. Exemplary rolls suitable for use herein may have diameters of about 6 to about 24 inches (15.24 to 60.96 cm), tooth pitch of about 0.030 to about 0.100 inch (0.762 to 2.54 mm), and tooth tip radius of about 0.004 to about 0.006 inch (0.102 to 0.152 mm).

Fabrication of Laminate

Figure 16:
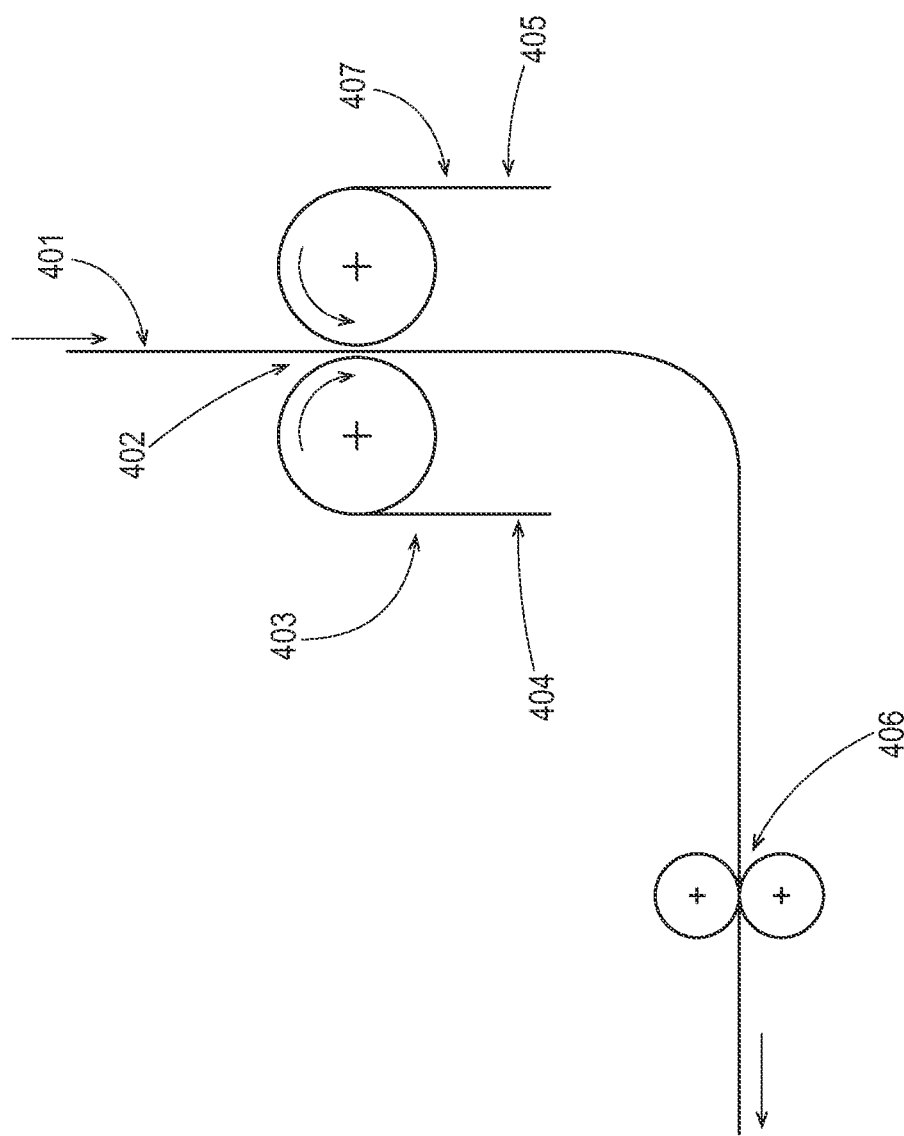
FIG. 16 is a schematic of the creation of a laminate in accordance with the present invention.

FIG. 16 shows an exemplary lamination process for a back ear laminate of the present invention. An adhesive applicator, 403, applies an adhesive to a first nonwoven web, 404, while another adhesive applicator, 403, applies an adhesive to a second nonwoven web, 405. Regardless of the type of hot melt adhesive, the adhesive immediately begins cooling after application to the nonwoven webs. The nonwovens, 404 and 405, are brought together at a nip, 402, with an elastic film, 401, positioned in between. The adhesive cools more after it is nipped into a laminate with the elastic film, and continues to cool as it makes its way to the ring roll. The nonwoven-film-nonwoven laminate is then taken to a ring roll, 406, where the laminate is activated.

Article

While the use of the stretch laminate is suggested in regard to certain regions of the absorbent article, it will be recognized that the stretch laminate may be used in other regions as well.

Figure 13:
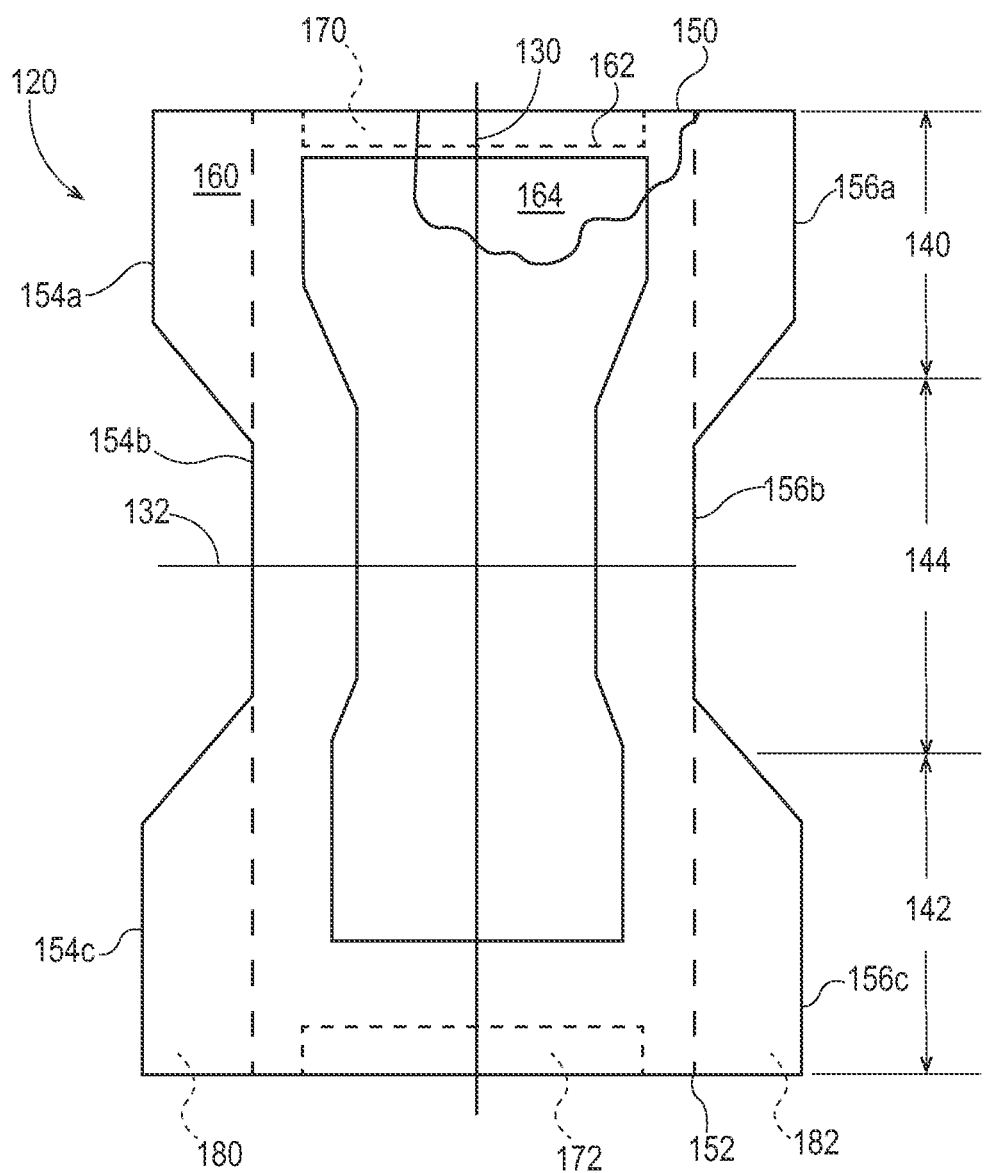
FIG. 13 is a plan view of an exemplary absorbent article including sections made of the stretch laminates of the present invention, with a section of a topsheet removed to expose an underlying absorbent core.

FIG. 13 is a plan view of an exemplary disposable absorbent article 120 in its flat, uncontracted state, i.e., without elastic-induced contraction. Portions of the article 120 have been cut away to more clearly show the underlying structure of the disposable absorbent article 120. As illustrated, the portion of the disposable absorbent article 20 that contacts the wearer faces the viewer (i.e., showing the interior or inner side of the article). The disposable absorbent article 120 has a longitudinal axis 130 and a transverse axis 132.

One end portion of the disposable absorbent article 120 is configured as a first waist region 140 of the disposable absorbent article 120. The opposite end portion is configured as a second waist region 142 of the disposable absorbent article 120. The waist regions 140 and 142 generally comprise those portions of the disposable absorbent article 120 which, when worn, encircle the waist of the wearer. The waist regions 140 and 142 may include elastic elements such that they gather about the waist of the wearer to provide improved fit and containment. An intermediate portion of the disposable absorbent article 120 is configured as a crotch region 144, which extends longitudinally between the first and second waist regions 140 and 142. The crotch region 144 is that portion of the disposable absorbent article 120 which, when the disposable absorbent article 120 is worn, is generally positioned between the legs of the wearer.

The disposable absorbent article 120 has a laterally extending first waist edge 150 in the first waist region 140 and a longitudinally opposing and laterally extending second waist edge 152 in the second waist region 142. The disposable absorbent article 120 has a first side edge 154 and a laterally opposing second side edge 156, both side edges extending longitudinally between the first waist edge 150 and the second waist edge 152. The portion of the first side edge 154 in the first waist region 140 is designated 154a, the portion in the crotch region 144 is designated 154b, and the portion in the second waist region 142 is designated 154c. The corresponding portions of the second side edge 156 are designated 156a, 156b, and 156c, respectively.

The disposable absorbent article 120 preferably comprises a water-permeable topsheet 160, a water-impermeable backsheet 162, and an absorbent assembly or core 164, which may be disposed between the topsheet 160 and the backsheet 162 with the topsheet 160 attached to the backsheet 162. The topsheet 160 may be fully or partially elasticized or may be foreshortened. Exemplary structures including elasticized or foreshortened topsheets are described in greater detail in U.S. Pat. Nos. 4,892,536; 4,990,147; 5,037,416; and 5,269,775, among others.

The absorbent article 120 may include at least one elastic waist feature 170 that helps to provide improved fit and containment. The elastic waist feature 170 may be intended to elastically expand and contract to dynamically fit the wearer's waist. The elastic waist feature 170 may extend at least longitudinally outwardly from at least one waist edge (e.g., edge 150) of the absorbent article 150 and generally forms at least a portion of the waist region (e.g., region 140) of the absorbent article 120. Diapers are often constructed so as to have two elastic waist features 170, 172, one (170) positioned in the first waist region 140 and one (172) positioned in the second waist region 142. Further, the elastic waist feature 170, 172 may be made of the stretch laminate 20 attached or joined to the backsheet 162. Alternatively, the elastic waist feature 170, 172 may be constructed as an extension of other elements of the absorbent article, such as the topsheet 160, the backsheet 162, or both the topsheet 160 and the backsheet 162 (e.g., the topsheet 160 or backsheet 162 defines one of the layers of the laminate). Other elastic waist feature constructions are described in U.S. Pat. Nos. 4,515,595; 4,710,189; 5,151,092; and 5,221,274.

The absorbent article 120 may include side panels 180, 182 attached to the backsheet 162. One or more of the side panels 180, 182 may be made from the stretch laminate. This construction may provide a more comfortable and contouring fit by initially conformably fitting the absorbent article 120 to the wearer, and sustaining this fit throughout the time of wear well past when the absorbent article 120 has been loaded with exudates, insofar as the elasticized side panels 180, 182 allow the sides of the absorbent article 120 to expand and contract. The side panels 180, 182 may also provide more effective application of the absorbent article 120 because even if the caretaker pulls one elasticized side panel 180 farther than the other (182) during application, the absorbent article 120 will "self-adjust" during wear. While the absorbent article 120 preferably has the side panels 180, 182 disposed in the second waist region 142, the absorbent article 120 may be provided with side panels disposed in the first waist region 140, or in both the front waist region 140 and the second waist region 142.

Figure 14:
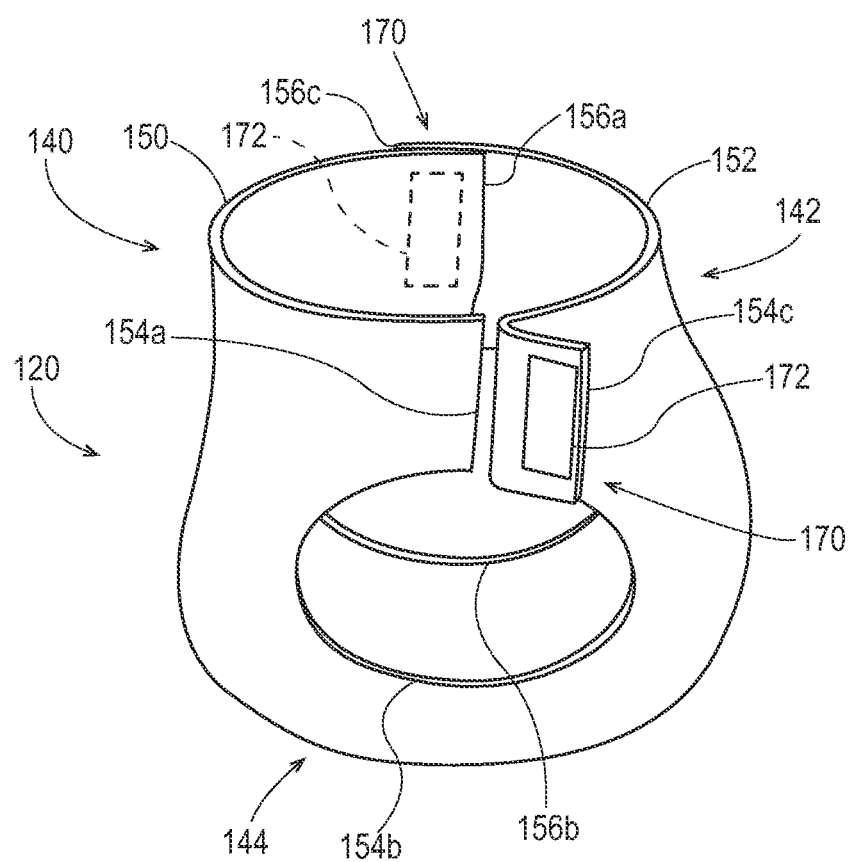
FIG. 14 is a perspective view of the absorbent article of FIG. 13 shown in its relaxed, contracted state, i.e., with the contraction induced by elastic members.

FIG. 14 illustrates the article illustrated in FIG. 13 configured to as it would be worn. The disposable absorbent article 120 may be sealed at the sides so as to be configured as illustrated in FIG. 13. However, the article 120 may instead include refastenable side seams 170 that can be used to fasten the waist regions 140, 142 together. According to one exemplary embodiment, the waist regions 140, 142 may be fastened at the sides to apply the article like a diaper. According to an exemplary embodiment, illustrated in FIG. 13, the side seams 170 may include fasteners 172 that can be used to configure the article like a pair of pull-on training pants or disposable pants.

As illustrated, the fasteners 172 may be disposed on the interior of the disposable absorbent article 120 in the second waist region 142 adjacent to the portion 154c of the first side edge 154 and adjacent to the portion 156c of the second side edge 156. The portion 154c of the side edge 154 is shown in an open condition, such as prior to closing and fastening or after being reopened. The portion 156c of the opposing side edge 156 is shown fastened, i.e., forming a pants configuration. In FIG. 13, the second waist region 142 overlaps the first waist region 140 when they are fastened together.

The fasteners 172 may be formed of any material and in any form that will releasably attach to the mating surface of the opposing waist region when pressed against it. For example, the primary fastening component may be a mechanical fastener that releasably engages with the mating surface, such as by means of a plurality of hooks engaging with loops formed by fibers in a nonwoven sheet. Alternatively, the primary fastening component may be an adhesive that releasably adheres to the mating surface. In fact, the fasteners may include tape tabs, hook and loop fastening components, interlocking fasteners such as tabs & slots, buckles, buttons, snaps, and/or hermaphroditic fastening components. Exemplary surface fastening systems are disclosed in U.S. Pat. Nos. 3,848,594; 4,662,875; 4,846,815; 4,894,060; 4,946,527; 5,151,092; and 5,221,274, while an exemplary interlocking fastening system is disclosed in U.S. Pat. No. 6,432,098. The fastening system may also include primary and secondary fastening systems, as disclosed in U.S. Pat. No. 4,699,622. Additionally exemplary fasteners and fastener arrangements, the fastening components forming these fasteners, and the materials that are suitable for forming fasteners are described in U.S. Published Application Nos. 2003/0060794 and 2005/0222546 and U.S. Pat. No. 6,428,526.

Still other variations are also possible. For example, the fasteners 172 may be disposed on the interior of the article 120 in the first waist region 140 such that the first waist region 140 overlaps the second waist region 142 when they are fastened together. As another example, the fasteners 170 may be disposed on the exterior of the article rather than on the interior. As a further example, the fasteners 170 may be used with a specific mating fastener surface particularly suited for cooperation with the fasteners 170 (e.g., a loop layer that works with a hook fastener, or a layer particularly treated to provide a suitable contacting surface for a specific adhesive).

Further nonlimiting examples of suitable absorbent articles for use with stretch laminates disclosed herein may be found in U.S. Pat. Nos. 3,860,003; 4,808,178; 4,909,803; 5,151,092; 5,221,274; 5,554,145; 5,569,234; 5,580,411; 6,004,306; 7,626,073; U.S. Publication No. 2007/0249254; and U.S. Ser. No. 13/026,563.

Examples

The following table, Table 3, shows examples of laminates that are subject to certain applied strains and applied strain rates and do not develop pin holes. Two different laminates are tested. The first type of laminate has a first nonwoven of 27 gsm, a second nonwoven of 17 gsm, and a 57 micron film in between, the film bonded to each nonwoven via a PO-based adhesive (laminates A and B). The second type of laminate has a first nonwoven of 24 gsm, a second nonwoven of 14 gsm, and a 57 micron film in between, the film bonded to each nonwoven via a PO-based adhesive (laminates C and D). As can be seen, even as the applied activation strain is 293%, none of the laminates form pin holes.

One or more examples are illustrated in the accompanying table, but those of ordinary skill in the art will understand that the laminates and articles described herein are non-limiting examples and embodiments and that the scope of the various non-limiting embodiments of the present disclosure are defined solely by the claims. The features illustrated or described in connection with one non-limiting embodiment or example may be combined with the features of other non-limiting embodiments or examples. Such modifications and variations are intended to be included within the scope of the present disclosure.

TABLE 3

Test Methods

| Example | A | B | C | D |
|---|---|---|---|---|
| Nonwoven #1 | 27 gsm Carded | 27 gsm Carded | 24 gsm Carded | 24 gsm Carded |
| Slot Coated Adhesive | PO-Based, 7 gsm | PO-Based, 7 gsm | PO-Based, 7 gsm | PO-Based, 7 gsm |
| Elastic Film | 57 micron SBS | 57 micron SBS | 51 micron SBS | 51 micron SBS |
| Slot Coated Adhesive | PO-Based, 4 gsm | PO-Based, 4 gsm | PO-Based, 4 gsm | PO-Based, 4 gsm |
| Nonwoven #2 | 17 gsm SMS | 17 gsm SMS | 14 gsm SMS | 14 gsm SMS |
| Applied Activation Strain | 250% | 293% | 250% | 293% |
| Applied Activation Strain Rate | 766 s^-1 | 851 s^-1 | 766 s^-1 | 851 s^-1 |
| Pinholes in Film | None | None | None | None |

Pin Holes

Stretch laminates are visually inspected for the presence of pin holes with the laminate stretched to 20% engineering strain (for example, a laminate of 100 mm width is stretched to 120 mm width). The defects are categorized by type, as either a "hole" or a "spot". A "hole" is defined as an area of the laminate in which the multilayer film has a complete failure, with the visual appearance of a hole or a tear. A "spot" is defined as an area of the laminate with a partial failure of the film, with the visual appearance of a hole or tear in some, but not all layers of the multilayered film. The largest dimension of each hole is measured with a steel rule, with the multilayered laminate stretched to 20% engineering strain under magnification (for example, using illuminated magnifier KFM 17113 available from LUXO, Elmsford, N.Y., 10523). The holes are categorized by size based on the length of the largest dimension of the hole; tiny (≤0.5 mm), small (>0.5 mm and ≤1 mm), medium (>1 mm and ≤2 mm), large (>2 mm and <3 mm) and extra large (>3 mm). When sufficient material is available, the number of holes per square meter of material (holes/m2) can be calculated. For example, 20 samples, each with a dimension of 100 mm by 100 mm, have a combined total area of 0.2 m2. The total number of holes in the 20 samples can be multiplied by five to calculate the number of holes/m2.

Tensile Test (Mode II Failure Force)

This method is used to determine the force versus engineering strain curve of multilayer laminates. The tensile properties of the materials were measured according to ASTM Method D882-02 with the specifications described below. The measurement is carried out at a constant crosshead speed of 50.8 cm/min at a temperature of 23° C.±2° C.

The relation between the material's deformed dimension and engineering strain is given by Engineering strain=(l−l0)/l0

Percent Engineering strain=engineering strain*100%

For example, when a sample with an initial gauge length of 50 mm is deformed to 90 mm, the engineering strain is (100−50)/50=1=100%. Or when a sample with an initial gauge length of 50 mm is deformed to 350 mm, the engineering strain is (350−50)/50=6=600%.

In some cases, it may not be possible to measure the Mode II failure force of the laminate, for example in cases where the sample breaks before the Mode II failure starts. If it is not possible to measure the Mode II failure force, the laminate bond strength can be measured by the T-Peel Test (Mode I) as follows:

T-Peel (Mode I) Test

The Mode I T-peel tensile test method is performed at room temperature (23° C.±2° C.). The material to be tested is cut into a substantially rectilinear shape. Sample dimensions are to be selected to achieve the required strain with forces appropriate for the instrument. Suitable sample dimensions are approximately 25.4 mm wide by approximately 100 mm long. Shorter specimens may be used, however, if material availability precludes specimens 100 mm in length. The length of the sample is the direction perpendicular to the axis of stretch. Suitable instruments, grips, grip faces, software for data acquisition, calculations, reports, and definition of percent strain are described in the Tensile Test (Mode II) method section above.

The load cell is selected so that the forces measured fall between 10% and 90% of the capacity of the load cell or the force range used. Typically a 25 N load cell is used. The fixtures and grips are installed. The instrument is calibrated according to the manufacturer's instructions. The distance between the lines of gripping force (gauge length as described in Tensile Test—Mode II) is 2.54 cm, which is measured with a steel ruler held beside the grips. The force reading on the instrument is zeroed to account for the mass of the fixture and grips. The samples are equilibrated at 23° C.±2° C. for a minimum of one hour before testing. The mass, length and width of the specimen are measured before sample preparation for the T-peel test and are used to calculate the basis weight of the specimen in grams per square meter (gsm). The samples (approximately 25.4 mm wide by approximately 100 mm long) are prepared for T-peel test using the following procedure: (1) Mark the sample with a pen, making a line across the 2.54 cm width of the sample at a location 2.54 cm from the end of the sample. (2) Stretch the sample in small increments in the 6.45 cm2 area between the pen mark and the end of the sample to initiate delamination of the nonwoven fibers from the film. (3) Secure a piece of masking tape (Corporate Express, MFG # CEB1X60TN, from Paperworks, Inc at pwi-inc.com or equivalent), 5.08 cm long and 2.54 cm wide, centered across the top 2.54 cm width of sample on the end of the sample which has been stretched to initiated delamination, Apply pressure to bond the tape to the sample. In the case of a bi-laminate, the tape is placed on the film surface. In the case of a tri-laminate, the tape is placed on the 2.54 cm wide surface opposite to the side for which the laminate bond strength is to be measured. This tape will support the film portion of the t-peel sample after steps 4 and 5 are complete. (4) Carefully pull the fibers off of the film on the side of the sample that does not have tape, in the 6.45 cm2 area between the pen mark and the end of the sample. For samples that are well bonded, this can be achieved by gently abrading the sample with a rubber eraser in the approximate direction toward the pen mark. (5) Carefully peel the nonwoven off of the film to the pen mark. (6) Place a second piece of tape, 5.08 cm long and 2.54 cm wide, centered across the top 2.54 cm width of the nonwoven fibers that have been intentionally delaminated from the sample to form the nonwoven portion of the T-peel sample. A minimum of five samples is used to determine the average test value. To perform the T-peel test, mount the sample into the grips in a T-peel configuration with the nonwoven portion of the T-peel sample mounted in the upper grip and the film portion of the T-peel sample mounted into the bottom grip. The specimen is mounted into the grips in a manner such that there is minimal slack and the force measured is less than about 0.02N. The crosshead moves up at a constant crosshead speed of 30.5 cm/min and the sample is peeled until the respective materials (nonwoven fibers and film) separate completely. The force and extension data are acquired at a rate of 50 Hz during the peel. The peak force (N/cm) during the first 50 mm of extension is reported as the Mode I peel force. Typical Mode I peel values for a well bonded laminate used in absorbent articles of the present invention are from about 1.0 N/cm to about 2.5 N/cm for non-activated samples and from about 0.5 N/cm to about 2.0 N/cm for activated samples.

Two Cycle Hysteresis Test

This method is used to determine properties that may correlate with the forces experienced by the consumer during application of the product containing the laminate and how the product fits once it is applied.

The two cycle hysteresis test method is performed at room temperature (23° C.±2° C.). The material to be tested is cut into a substantially rectilinear shape. Sample dimensions are selected to achieve the required strain with forces appropriate for the instrument. Suitable sample dimensions are approximately 25.4 mm wide by approximately 76.2 mm long. Shorter specimens may be used, however, if material availability precludes specimens 76.2 mm in length. The sample is selected and mounted such that the direction of elongation in the test method is perpendicular to the width of the sample, such that it can be elongated to a length of at least the maximum percent strain of the hysteresis test. Suitable instruments, grips, grip faces, software for data acquisition, calculations and reports and definition of percent strain are described in the Tensile Test (Mode II) method section above.

The load cell is selected so that the forces measured fall between 10% and 90% of the capacity of the load cell or the force range used. Typically a 25 N or 100N load cell is used. The fixtures and grips are installed. The instrument is calibrated according to the manufacturer's instructions. The distance between the line of gripping force (gauge length, as described in the Tensile test-Mode II) is 2.54 cm, which is measured with a steel ruler held beside the grips. The force reading on the instrument is zeroed to account for the mass of the fixture and grips. The samples are equilibrated at 23° C.±2° C. for a minimum of one hour before testing. The mass, length and width of the specimen are measured before testing and are used to calculate the basis weight of the specimen in grams per square meter (gsm). A minimum of five samples is used to determine the average test values. The specimen is mounted into the grips in a manner such that there is minimal slack and the force measured is less than 0.02N. The first segment of the two cycle hysteresis test method is a gauge adjustment step using a 5 gram preload slack adjustment. The engineering tensile engineering strain $\gamma_{tensile}$ is defined in the Tensile Test Method section above and with a slack adjustment preload segment, Lo is the adjusted gauge length, L is the stretched length and $\gamma_{tensile}$ is in units of percent. The Two Cycle Hysteresis Test is done using the following segments:

(1) Slack adjustment: Move the crosshead at 13 mm/min. until the specified 5 gf slack adjustment preload is achieved. The distance between the lines of gripping force at the 5 gf slack adjustment preload is the adjusted gauge length.

(2) Move the crosshead to achieve the specified percent engineering strain (i.e., engineering strain=130%) at a constant crosshead speed of 254 mm/min. For example, if the adjusted gauge length from segment 1 is 26.00 mm, the sample is stretched to 59.80 mm and the % engineering strain=((59.80/26.00)−1)*100=130%.

(3) Hold the sample for 30 seconds at the specified percent engineering strain (i.e., engineering strain=130%).

(4) Reduce engineering strain to 0% engineering strain (i.e., return grips to adjusted gauge length) at a constant crosshead speed of 254 mm/min.

(5) Hold the sample for 60 seconds at 0% engineering strain. (segments 1 to 5 complete Cycle 1)

(6) Repeat segments 2 through 5 to complete the second cycle of the Two Cycle Hysteresis Test.

The method reports Cycle 1 load forces at 100% engineering strain and 130% engineering strain (from segment 2), Cycle 1 unload force at 50% engineering strain and 30% engineering strain (from segment 4), percent set and force relaxation. The forces are reported in N/cm, where cm is the width of the sample. The percent set is defined as the percent engineering strain after the start of the second load cycle (from segment 6) where a force of 7 grams is measured (percent set load=7 grams). Force relaxation is the reduction in force during the hold in segment 3 and is reported as a percent. Percent force relaxation is calculated from the forces measured at 130% engineering strain during Cycle 1 and is equal to 100*[((initial force at 130% engineering strain)−(force at 130% engineering strain after the 30 second hold))/(initial force at 130% engineering strain)].

For different sample dimensions, the crosshead speed is adjusted to maintain the appropriate strain rate for each portion of the test. For example; a crosshead speed of 127 mm/min would be used in segments 2, 4 and 6 for a sample gauge length of 12.7 mm and a crosshead speed of 381 mm/min would be used in segments 2, 4 and 6 for a sample gauge length of 38.1 mm. Additionally, for samples with different widths, the slack preload force (5 grams per 2.54 cm width=1.97 g/cm) and the percent set load force (7 grams per 2.54 cm width=2.76 g/cm) must be adjusted for the different sample width. The Two Cycle Hysteresis Test may also be modified depending on the expected properties of the material tested. For example, if the sample is not capable of being elongated to 130% engineering strain without breaking, the sample is to be elongated to 100% engineering strain. And, if the sample is not capable of being elongated to 100% engineering strain, the sample is to be elongated to 70% engineering strain. In the latter two cases (elongation to 100% or 70% strain), force relaxation is determined at the maximum elongation of Cycle 1 as defined above for elongation of 130% engineering strain. The Two Cycle Hysteresis Test may also be modified to enable measurement of hysteresis forces of a laminate after stretching to a higher engineering strain by using a specified percent engineering strain of 165% or 200%. This may be useful when the laminate of the absorbent article stretches to 165% engineering strain, or to 200% engineering strain during application or use.

Permanent Set

See the Two Cycle Hysteresis Test Immediately Above.

Percent Strain Recovery Test (PSRT)—

The Percent Strain Recovery Test (PSRT), is used to quantify how a material recovers after deformation, as it relates to post activation set (e.g. how does the dimension of the material change due to activation). The Two Cycle Hysteresis Test above was modified by (1) eliminating the 30 second hold in step 3 at the specified maximum engineering strain and by (2) testing material at several maximum percent engineering strains (100%, 200%, 245% and 324%), including higher strains similar to strains used for activation. Fresh samples are used for each maximum percent engineering strain tested. The percent set is defined as the percent engineering strain after the start of the second load cycle (from segment 6) where a force of 7 grams is measured (percent set load=7 grams). The result reported, Percent Recovery of Strain (PRS), is calculated using the equation below:

PRS=100×[1−(percent set/maximum percent engineering strain)]

The PRS is reported for each maximum strain tested.

G'norm

Equipment for Dynamical Mechanical Analysis (DMA) Determination of G' Kinetics Upon Cooling:

DHR3 Rheometer by TA Instruments as described below

Balance

Figure 17:
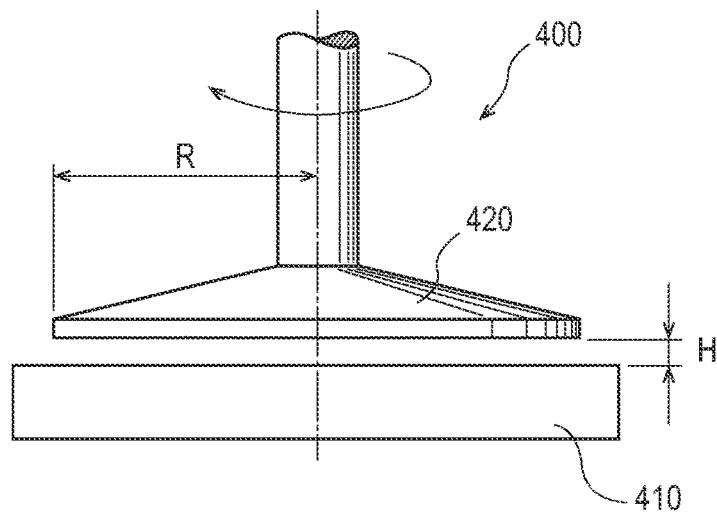
FIG. 17 is a schematic representation of a rheometer that may be used in a test method of the present invention.

Rheometer:

A test set up for analyzing G' versus time during and after cooling utilizes the DHR3 Rheometer by TA Instruments as described herein. Other rheometers are available on the market, which yield substantially the same test results. FIG. 17 provides a schematic representation of the rheometer (400). The rheometer is capable of applying an oscillatory shear stress to the adhesive and measuring the resulting strain (shear deformation) response at constant temperature. The rheometer is capable of applying a small amplitude of oscillatory stress to achieve a constant oscillatory strain (e.g., 0.05% at 10 rad/s) within the linear viscoelastic region of the adhesive. The rheometer is capable to control axial force (Normal Force) to keep the axial stress low (0.0N+/−0.1N) by adjusting the gap (H) to compensate for axial thermal shrinking of the sample during cooling. The instrument enables the measurement of resulting Storage Modulus, Loss Modulus and the phase shift between stress and strain (Loss Factor) in dependence of temperature which can be controlled by a Peltier element. The Peltier element acts as lower, fixed plate (410) and an upper plate (420) with a radius R of 10 mm, which is connected to the drive shaft of a motor, generates the applied oscillatory shear stress. The initial gap at 150° C. between both plates has a height H of 1000 microns. The lower fixed plate (410) incorporates a temperature probe for determining the plate and sample temperature, and controlling the temperature of the material (±0.5° C.) by the Peltier-element.

Sample Preparation:

Homogenize the adhesive at 150° C.-175° C. (depending on type of adhesive) for 1 hour in a lab oven. Stir occasionally to ensure proper mixing of the adhesive, but prevent formation of air bubbles. After homogenization in the oven pour the sample on silicone paper for cooling. After the material is cooled to RT, weigh approximately 0.4 g of adhesive for the test and place the material on the Peltier-plate.

Test Execution:

Melt the adhesive at 150° C. (or higher if necessary) on the Peltier-plate. As soon as the adhesive is completely molten, lower the upper plate to a gap of 1000 microns to bring it into proper contact with the adhesive melt. Remove excessive material and set the temperature to the measurement start temperature (e.g., 150° C., depending on the lamination process application temperature).

Set the normal force control (e.g., 0N+/−0.1N). Condition the sample at 150° C. for 120 seconds, apply then a per-shear for 120 seconds with a constant shear rate of 2.5 1/s to homogenize the sample on the rheometer and finally condition it then again at 150° C. for 120 s without shear to ensure thermal equilibrium between peltier, adhesive, and upper plate.

Set the constant oscillatory measurement target strain (e.g., 0.05%) or stress. Set the constant frequency (e.g., 10 rad/s).

Set the maximum cooling rate (e.g., >20° C./min) for a target temperature below the softening point of the adhesive and well-below the lamination application process temperature. Begin the oscillation scanning at the initial application temperature and immediately execute the cooling step. Collect G' and temperature as a function of time and continue collecting data after thermal equilibrium is achieved and G' is stable, e.g., 1 hour total collection time, 150° C. initial temperature, 60° C. final target temperature, 27° C./min cooling rate. The amount of time needed to reach equilibrium may be more or less depending on the cooling capability of the instrument or the thermal mass of the instrument's plate geometry and the amount and heat capacity of adhesive on the rheometer.

After the test is completed, melt the adhesive, lift the upper plate and remove the adhesive from both Peltier and upper plate. Set the temperature back to RT.

Result Reporting:

Report the Normalized Storage Modulus $G'_{Norm}$ by using the following equation:

$$G'_{Norm} = \frac{(G'_t - G'_0)}{(G'_\infty - G'_0)}$$

Where $G'_t$ is the storage modulus measured as a function of time, $G'_0$ is the storage modulus at the initial temperature of the scan at t=0 (e.g., at 150° C. application temperature), and $G'_\infty$ is the equilibrated storage modulus at the lower target temperature of the scan, once equilibrium has been achieved, i.e., no appreciable change in the storage modulus is observed with time at the target temperature, e.g., after one hour since initiating the cooling.

Laminate Test for Force vs Extension

MTS Reliance Tensile Tester with 100N load cell.

Sample size: rectangular 25.4 mm wide, 31.8 mm long.

Gauge length set to 25.4 mm

Crosshead speed set to 4.233 mm/sec.

Time, crosshead displacement, and load data were collected at an even rate that generated ten points per mm of displacement.

Figure 19:
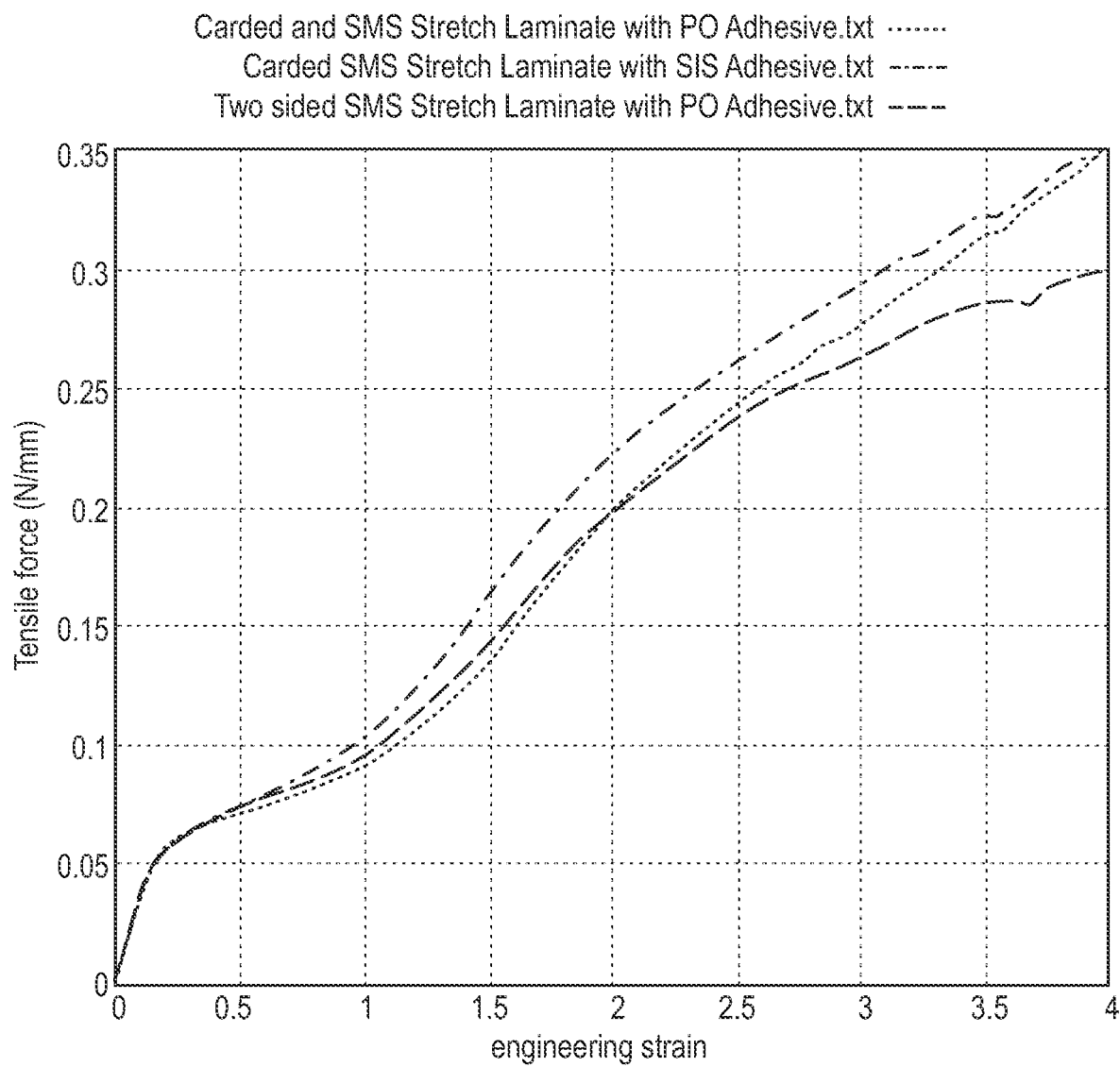
FIG. 19 is a graph of tensile force vs. engineering strain.

As shown in FIG. 19, in the region of the graph where engineering strain is from 0 to 1, the tensile response to the applied strain comes primarily from the elastic film. Stretch performance is unhindered. As strain increases, into the middle region on the graph where engineering strain is from about 1 to 2 (100% to 200% engineering strain), there is a more rapid increase in the tensile response. The nonwovens increasingly contribute to the mechanical response. This is known as the "force-wall," where the laminate feels like it has reached its limit. We can broadly define this "force-wall" region as a maximum in the slope of the tensile curve that occurs in the strain region after about 0.5 engineering strain and before about 3.5 engineering strain. In the right region, where there is more than 2 engineering strain, the strain past the force-wall initiates mechanical failure of the nonwovens and the nonwoven/film laminate interfaces. To locate the tensile curve's maximum, one can pick the middle of the region, i.e., 0.15 N/mm of stretch force at 150% applied strain.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising at least one stretchable laminate comprising a first nonwoven, a second nonwoven, and an elastic film therebetween; wherein each of the first and second nonwovens is adhesively bonded to the film by a polyolefin-based hot melt adhesive; wherein the film is no thicker than about 60 micrometers; wherein at least one of the nonwovens is a spunbond nonwoven; wherein the laminate is activated with a minimum of about 290% applied strain and a minimum strain rate of 1,000/s; wherein the laminate is substantially free from pinholes; wherein activation occurs before the adhesive achieves 85% of its normalized modulus G'; wherein the normalized modulus G' of the polyolefin-based hot melt adhesive has a normalized modulus G' maximum value; wherein the normalized modulus G' of the polyolefin-based hot melt adhesive is from about 30% to about 70% of the normalized modulus G' maximum value at 250 seconds; wherein the adhesive comprises interpolymers of ethylene comprising at least one comonomer selected from vinyl esters of saturated carboxylic acid wherein the acid moiety has up to 4 carbon atoms, unsaturated mono- or dicarboxylic acids of 3-5 carbon atoms, a salt of the unsaturated acid, esters of the unsaturated acid derived from an alcohol having 1 to 8 carbon atoms, and mixtures thereof; wherein the adhesive comprises 0% by weight of a tackifying resin; wherein the laminate comprises a plurality of raised rib-like elements separated by unformed areas; and wherein the elastic film comprises a SBS block copolymer.

2. The absorbent article of claim 1, further comprising at least one of a side panel, an outer cover, a back ear, and a waistband that comprises at least one stretchable laminate.

3. The absorbent article of claim 1, wherein the second nonwoven is carded.

4. The absorbent article of claim 1, wherein both the first and second nonwovens are spunbond nonwovens.

5. The absorbent article of claim 1, wherein at least one of the nonwovens is extensible.

6. The absorbent article of claim 1, wherein at least one of the nonwovens comprises bicomponent fibers.

7. The absorbent article of claim 1, wherein the spunbond nonwoven has a basis weight of at most about 17 gsm.

8. The absorbent article of claim 3, wherein the carded nonwoven has a basis weight of at most about 27 gsm.

9. The absorbent article of claim 1, wherein activation occurs before the adhesive achieves 95% of its normalized modulus G'.

10. The absorbent article of claim 1, wherein the laminate is activated with a minimum of about 300% applied strain.

11. The absorbent article of claim 1, wherein the adhesive's G'norm, measured at 1 minute after the adhesive is applied to the nonwoven, is at most about 0.2.

12. The absorbent article of claim 1, comprising a longitudinal axis and a transverse axis, wherein the plurality of raised rib-like elements have a first dimension substantially parallel to the longitudinal axis that is longer than a second dimension substantially parallel to the transverse axis.

13. An absorbent article comprising a first waist region, a second waist region, a crotch region disposed between the first and second waist regions, and side ears extending from the second waist region comprising at least one stretchable laminate comprising a first nonwoven, a second nonwoven, and an elastic film therebetween; wherein each of the first and second nonwovens is adhesively bonded to the film by a polyolefin-based hot melt adhesive; wherein the adhesive comprises interpolymers of ethylene comprising at least one comonomer selected from vinyl esters of saturated carboxylic acid wherein the acid moiety has up to 4 carbon atoms, unsaturated mono- or dicarboxylic acids of 3-5 carbon atoms, a salt of the unsaturated acid, esters of the unsaturated acid derived from an alcohol having 1 to 8 carbon atoms, and mixtures thereof; wherein the adhesive comprises 0% by weight of a tackifying resin; wherein at least one of the nonwovens is a spunbond nonwoven; wherein the laminate is activated with a minimum of about 290% applied strain and a minimum strain rate of 1,000/s; wherein the laminate is substantially free from pinholes; wherein activation occurs before the adhesive achieves 85% of its normalized modulus G'; wherein the normalized modulus G' of the polyolefin-based hot melt adhesive has a normalized modulus G' maximum value; wherein the normalized modulus G' of the polyolefin-based hot melt adhesive is from about 30% to about 70% of the normalized modulus G' maximum value at 250 seconds; wherein the laminate comprises raised rib-like elements separated by unformed areas; and wherein the elastic film comprises a SBS block copolymer.

14. The absorbent article of claim 13, comprising a longitudinal axis and a transverse axis, wherein the raised rib-like elements have a first dimension substantially parallel to the longitudinal axis that is longer than a second dimension substantially parallel to the transverse axis.

15. An absorbent article comprising a longitudinal axis, a transverse axis, a first waist region, a second waist region, a crotch region disposed between the first and second waist regions, side ears extending from the second waist region, a stretchable laminate comprising a first nonwoven, a second nonwoven, and an elastic film therebetween; wherein each of the first and second nonwovens is adhesively bonded to the film by a polyolefin-based hot melt adhesive; wherein the adhesive comprises interpolymers of ethylene comprising at least one comonomer selected from vinyl esters of saturated carboxylic acid wherein the acid moiety has up to 4 carbon atoms, unsaturated mono- or dicarboxylic acids of 3-5 carbon atoms, a salt of the unsaturated acid, esters of the unsaturated acid derived from an alcohol having 1 to 8 carbon atoms, and mixtures thereof wherein the adhesive comprises 0% by weight of a tackifying resin; wherein at least one of the nonwovens is a spunbond nonwoven; wherein the stretchable laminate is activated with a minimum of about 290% applied strain and a minimum strain rate of 1,000/s; wherein the stretchable laminate is substantially free from pinholes; wherein activation occurs before the adhesive achieves 85% of its normalized modulus G'; wherein the normalized modulus G' of the polyolefin-based hot melt adhesive has a normalized modulus G' maximum value; wherein the normalized modulus G' of the polyolefin-based hot melt adhesive is from about 30% to about 70% of the normalized modulus G' maximum value at 250 seconds; wherein the stretchable laminate comprises raised rib-like elements separated by unformed areas; wherein the raised rib-like elements have a first dimension substantially parallel to the longitudinal axis that is longer than a second dimension substantially parallel to the transverse axis and wherein the elastic film comprises a SBS block copolymer.

16. The absorbent article of claim 15, wherein the side ears comprise the stretchable laminate.

* * * * *